United States Patent
Dong et al.

(10) Patent No.: US 12,233,096 B2
(45) Date of Patent: Feb. 25, 2025

(54) RECOMBINANT REPLICATION COMPETENT VIRUSES COMPRISING A CODING REGION FOR GLYCOGEN SYNTHASE KINASE-3 (GSK3) AND METHODS OF KILLING ABERRANT CELLS

(71) Applicant: ORCA Therapeutics B.V., s-Hertogenbosch (NL)

(72) Inventors: Wenliang Dong, Almere (NL); Tanja Denise De Gruijl, Amsterdam (NL); Marta López González, Amsterdam (NL); Victor Willem Van Beusechem, Amstelveen (NL)

(73) Assignee: ORCA Therapeutics B.V., 's-Hertogenbosch (NL)

( * ) Notice: Subject to any disclaimer, the term of this patent is extended or adjusted under 35 U.S.C. 154(b) by 861 days.

(21) Appl. No.: 17/271,287

(22) PCT Filed: Aug. 30, 2019

(86) PCT No.: PCT/NL2019/050562
§ 371 (c)(1),
(2) Date: Feb. 25, 2021

(87) PCT Pub. No.: WO2020/046130
PCT Pub. Date: Mar. 5, 2020

(65) Prior Publication Data
US 2021/0205383 A1    Jul. 8, 2021

(30) Foreign Application Priority Data
Aug. 31, 2018   (EP) ..................... 18192104

(51) Int. Cl.
*A61K 35/761*   (2015.01)
*A61K 38/45*   (2006.01)
*C12N 15/86*   (2006.01)

(52) U.S. Cl.
CPC ............ *A61K 35/761* (2013.01); *A61K 38/45* (2013.01); *C12N 15/86* (2013.01); *C12N 2710/10332* (2013.01); *C12Y 207/11026* (2013.01)

(58) Field of Classification Search
CPC ...... A61K 35/761; A61K 38/45; C12N 15/86; C12N 2710/10332; C12N 9/12; C12N 2710/10043; C12Y 207/11026; A61P 35/00
See application file for complete search history.

(56) References Cited

U.S. PATENT DOCUMENTS

2003/0114382 A1*  6/2003  Walsh ................ A61P 43/00
                                              435/7.1
2011/0318311 A1* 12/2011  Reid ................. C12N 15/86
                                              435/235.1

FOREIGN PATENT DOCUMENTS

| JP | 2007522797 A | 8/2007 |
| JP | 2018-509914 A | 4/2018 |
| WO | 2010101921 A2 | 9/2010 |
| WO | 2016146894 A1 | 9/2016 |

OTHER PUBLICATIONS

Seven Hills Bioreagents. Ad5-CMV-AKT Vector. https://www.sevenhillsbioreagents.com/collections/adenoviral-vectors/products/ad5-cmv-akt. Rev. Oct. 19, 2007. (Year: 2007).*
Summers SA, Kao AW, Kohn AD, Backus GS, Roth RA, Pessin JE, Birnbaum MJ. The role of glycogen synthase kinase 3beta in insulin-stimulated glucose metabolism. J Biol Chem. Jun. 18, 1999;274(25):17934-40. (Year: 1999).*
"GSK3B". The Human Protein Atlas. https://www.proteinatlas.org/ENSG00000082701-GSK3B/tissue. Accessed Oct. 3, 2024. (Year: 2024).*
Cole AR, Sutherland C. Measuring GSK3 expression and activity in cells. Methods Mol Biol. 2008;468:45-65. (Year: 2008).*
Kim et al.; "Regulation of Angiogenesis by Glycogen Synthase Kinase-3beta", The Jounal of Biological Chemistry. vol. 277, No. 44, Issue of Nov. 1, 2002, pp. 41888-41896.
Li et al.; "Glycogen synthase kinase 3beta induces apoptosis in cancer cells through increase of survivin nuclear ocalization", Elsevier, Cancer Letters 272 (2008), pp. 91-101.
Shen et al. "Glycogen Synthase Kinase-3Beta Suppresses Tumor Necrosis Factor-Alpha Expression in Cardiomyocytes During lipopolysaccharide Stimulation" Journal of Cellular Biochemistry 104:329-338 (2008).
Kai et al. "GSK3beta plays pro-fibrogenic activity through TGF-beta /Smad signaling pathway in renal tubular epithelial cells" J Third Mil Med Univ, vol. 34, No. 19, pp. 1921-1923.
Ye et al. "ERK/GSK3beta signaling is involved in atractylenolide I-induced apoptosis and cell cycle arrest in melanoma cells" Oncology Reports, vol. 34, pp. 1543-1548.

* cited by examiner

*Primary Examiner* — Rachel B Gill
(74) *Attorney, Agent, or Firm* — Banner & Witcoff, Ltd.

(57) ABSTRACT

The invention in one aspect relates to recombinant replication competent adenovirus that can replicate in and lyse a host cell comprising in the genome of the adenovirus a coding sequence for a glycogen synthase kinase-3 (GSK3) protein operably linked to an expression control sequence. It also relates, among others, to means and methods for treatment of cancer with a coding sequence for a glycogen synthase kinase-3 (GSK3) protein operably linked to an expression control sequence, preferably in the context of an adenovirus. This work was funded in part by European Union Horizon 2020 research and innovation programme, Marie-Sklodowska-Curie grant number 643130.

15 Claims, 13 Drawing Sheets
Specification includes a Sequence Listing.

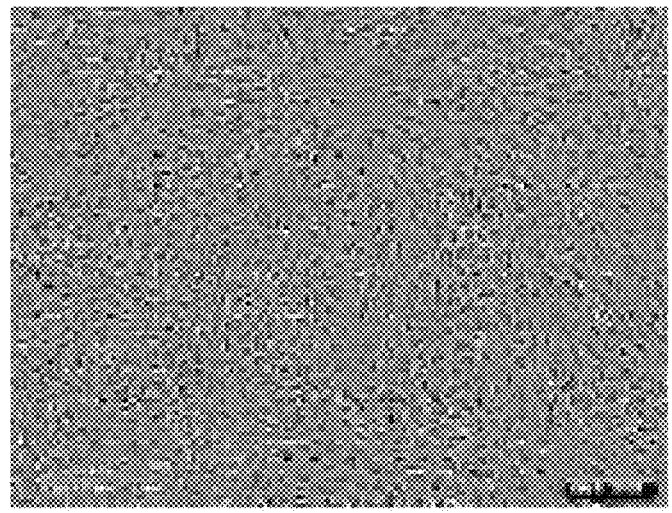
Ad.LUC
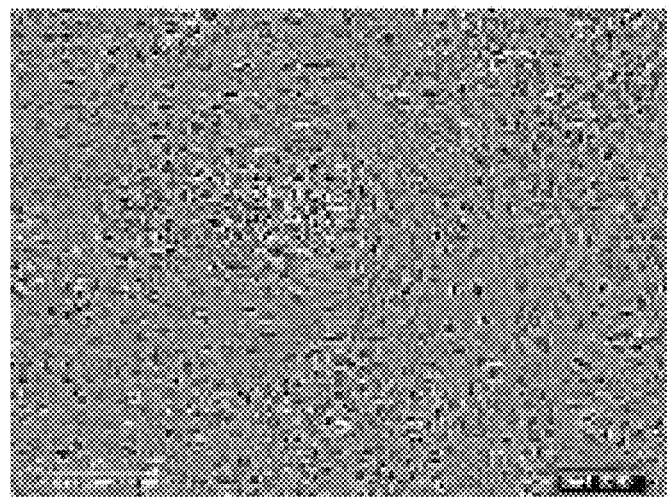
Ad.CA.GSK3β
Fig. 1C

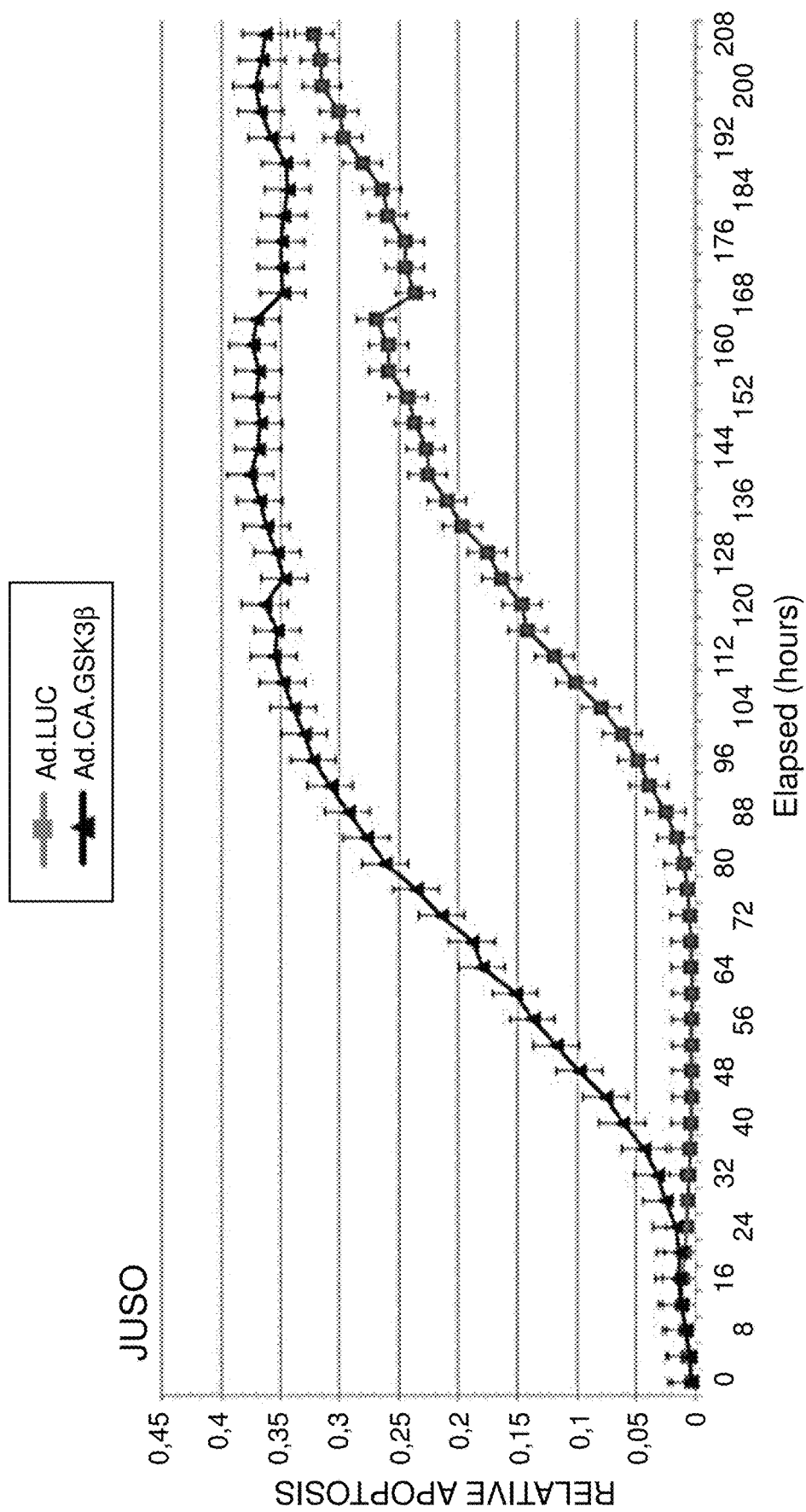
Fig. 2B, Cont'd

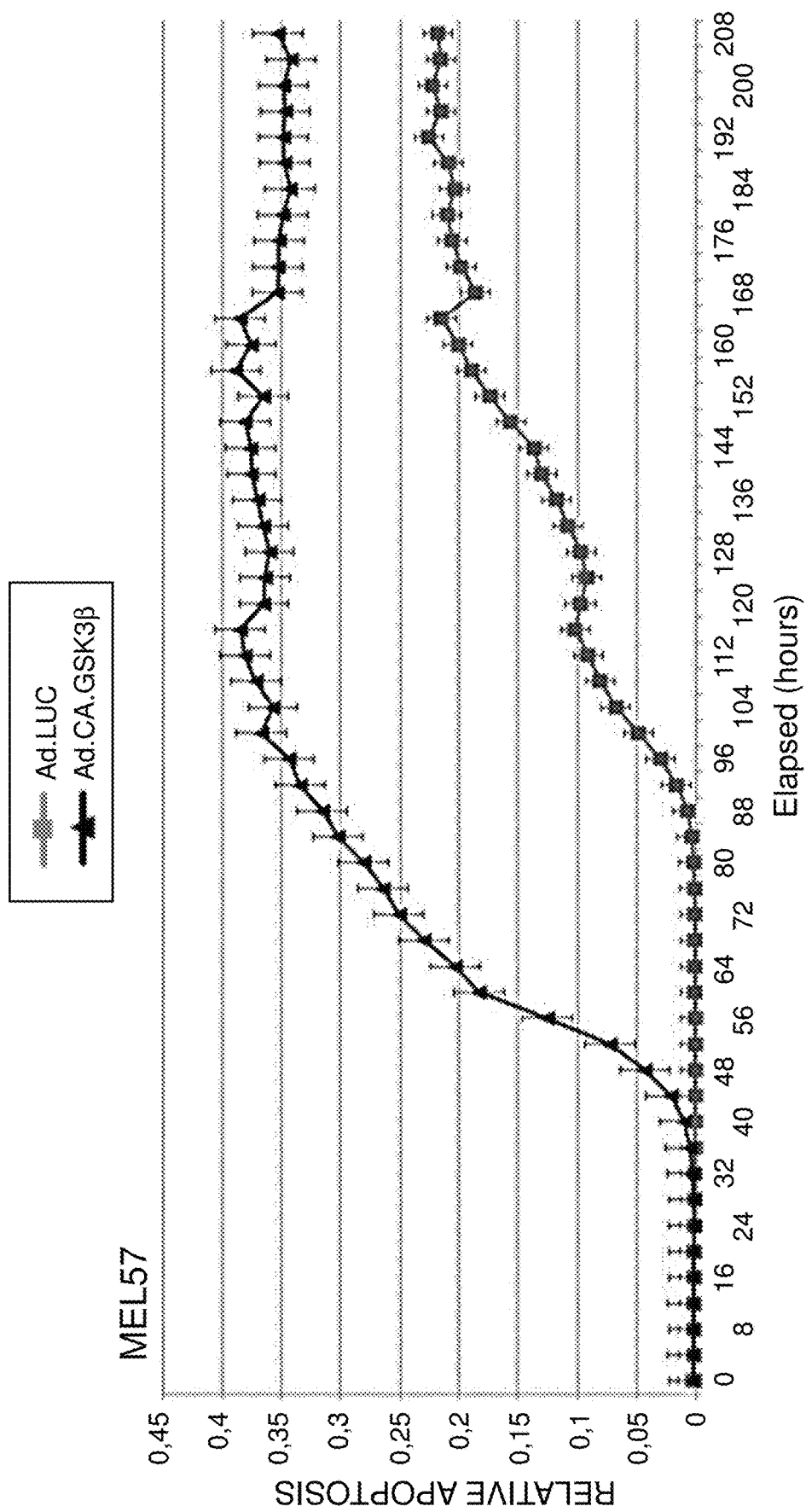
Fig. 2B, Cont'd

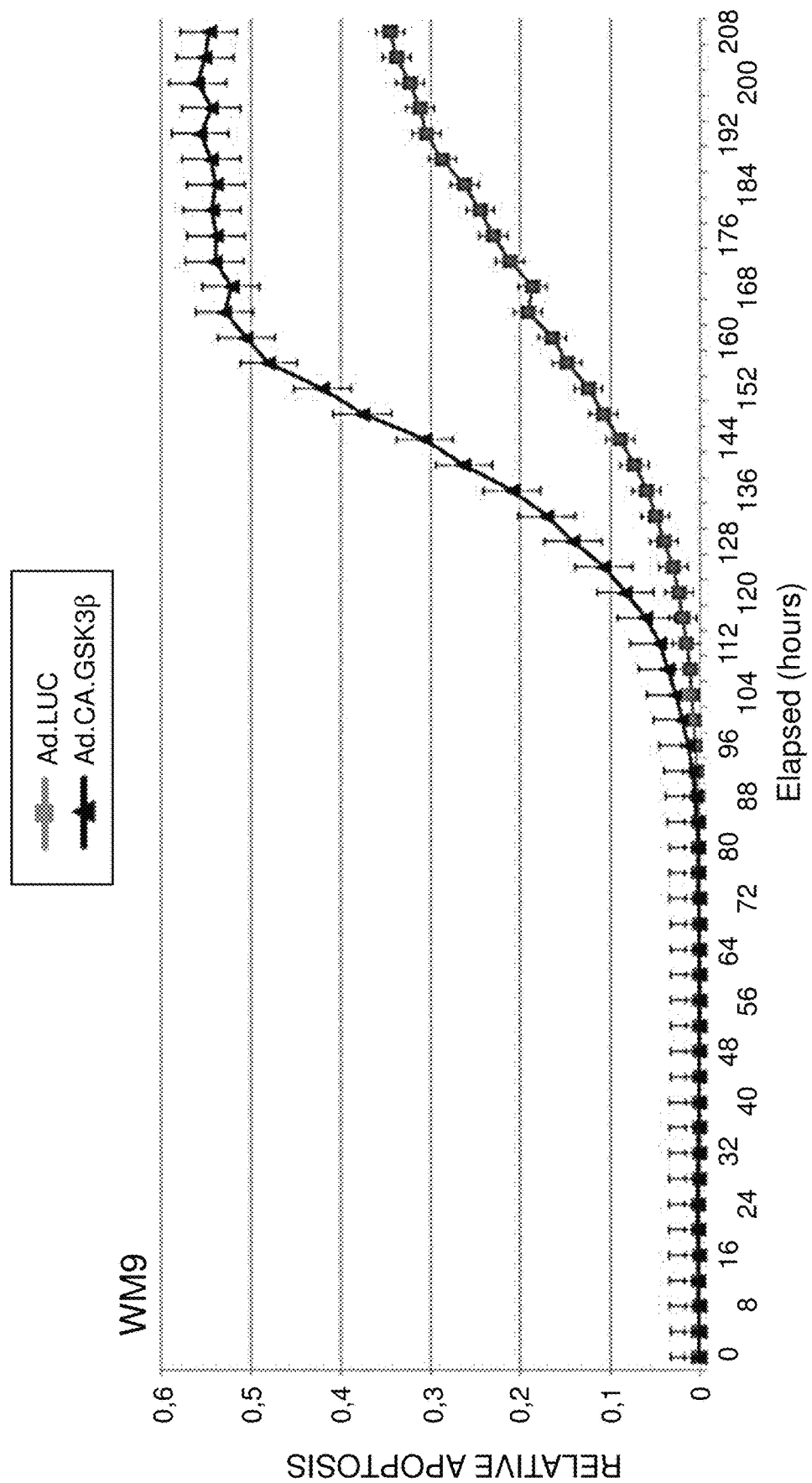
Fig. 2B, Cont'd

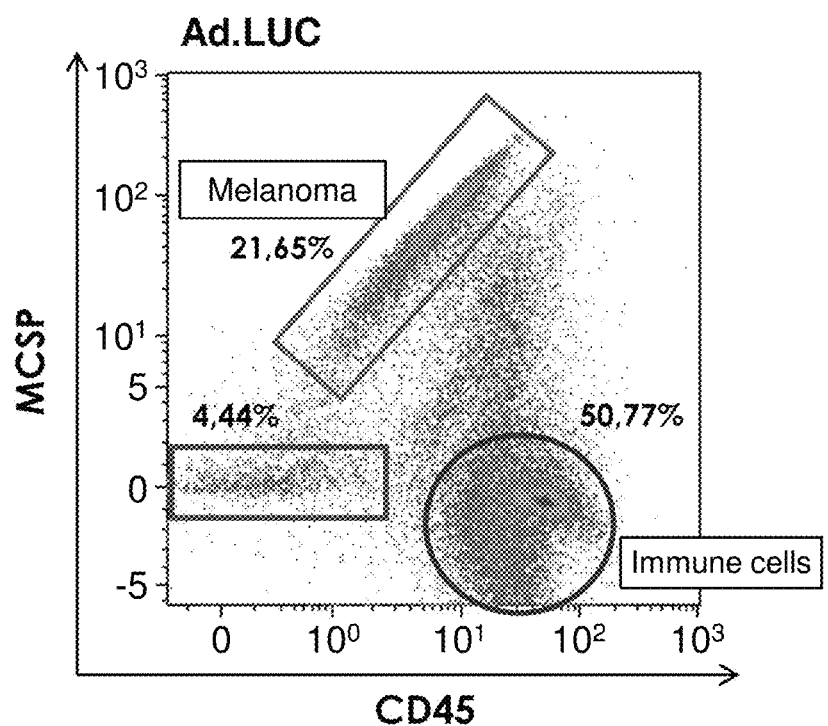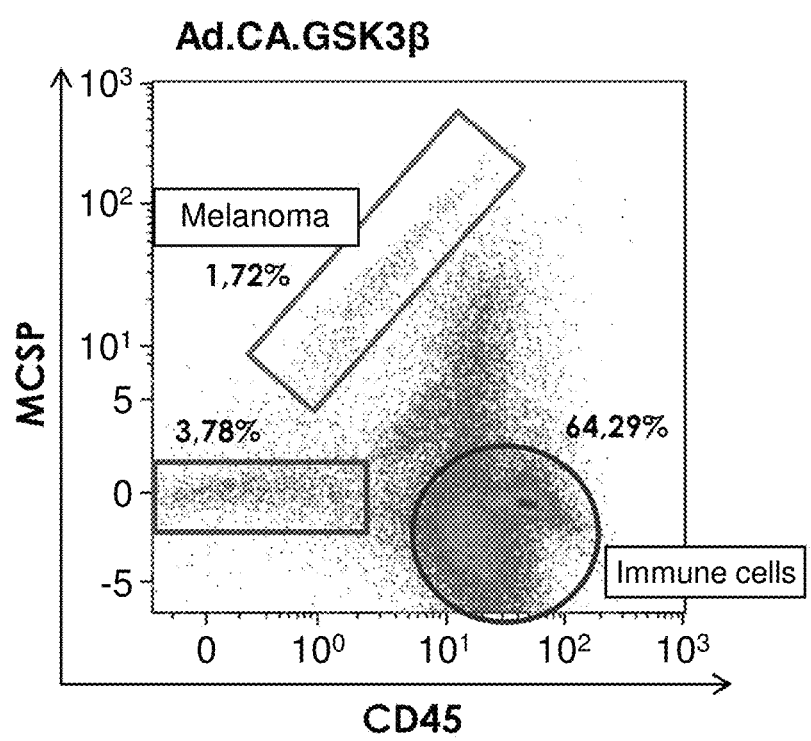
Fig. 3

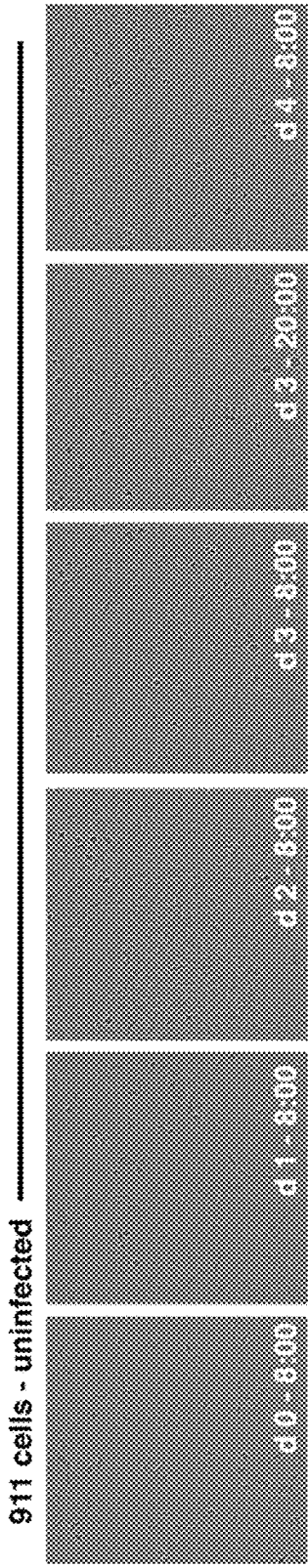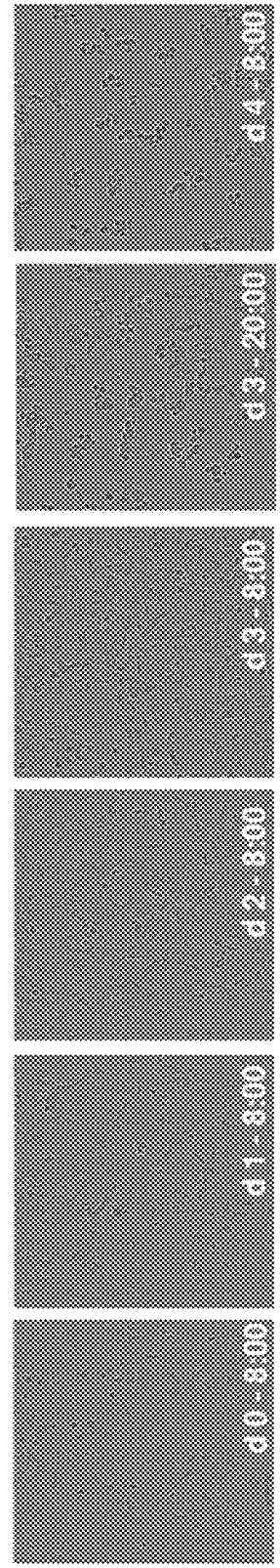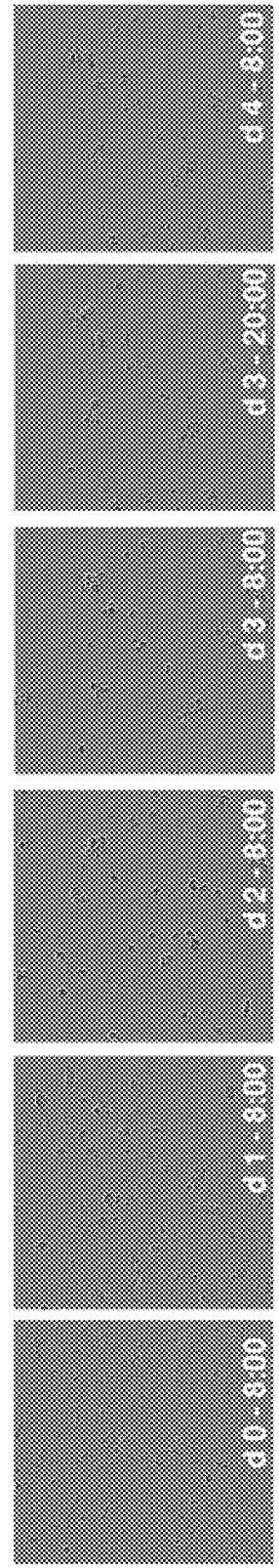

SEQUENCE LISTING

<160> NUMBER OF SEQ ID NOS: 16

<210> SEQ ID NO 1
<211> LENGTH: 484
<212> TYPE: DNA
<213> ORGANISM: Artificial Sequence
<220> FEATURE:
<223> OTHER INFORMATION: Mutant of codifying region for protein E3-19K of human adenovirus serotype 5

<400> SEQUENCE: 1

```
atgattaggt acataatcct aggtttactc acccttgcgt cagcccacgg taccacccaa      60
aaggtggatt ttaaggagcc agcctgtaat gttacattcg cagctgaagc taatgagtgc     120
accactctta taaaatgcac cacagaacat gaaaagctgc ttattcgcca caaaaacaaa     180
attggcaagt atgctgttta tgctatttgg cagccaggtg acactacaga gtataatgtt     240
acagttttcc agggtaaaag tcataaaact tttatgtata cttttccatt ttatgaaatg     300
tgcgacatta ccatgtacat gagcaaacag tataagttgt ggccccccaca aaattgtgtg    360 gaaaacactg gcactttctg ctgcactgct atgctaatta cagtgctcgc tttggtctgt    420
accctactct atattaaata caaaaagcag acgcagcttt attgaggaaa agaaaatgcc    480
ttaa                                                                  484
```

<210> SEQ ID NO 2
<211> LENGTH: 7
<212> TYPE: PRT
<213> ORGANISM: Artificial Sequence
<220> FEATURE:
<223> OTHER INFORMATION: Fragment of mutated carboxy-terminal fragment of protein E3-19K of human adenovirus type 5

<400> SEQUENCE: 2

```
Lys Lys Gln Thr Gln Leu Tyr
 1               5
```

<210> SEQ ID NO 3
<211> LENGTH: 483
<212> TYPE: DNA
<213> ORGANISM: Artificial Sequence
<220> FEATURE:
<223> OTHER INFORMATION: Mutant of codifying region for protein E3-19K of human adenovirus type 5

<400> SEQUENCE: 3

```
atgattaggt acataatcct aggtttactc acccttgcgt cagcccacgg taccacccaa      60
aaggtggatt ttaaggagcc agcctgtaat gttacattcg cagctgaagc taatgagtgc     120
accactctta taaaatgcac cacagaacat gaaaagctgc ttattcgcca caaaaacaaa     180
attggcaagt atgctgttta tgctatttgg cagccaggtg acactacaga gtataatgtt     240
acagttttcc agggtaaaag tcataaaact tttatgtata cttttccatt ttatgaaatg     300
tgcgacatta ccatgtacat gagcaaacag tataagttgt ggccccccaca aaattgtgtg    360 gaaaacactg gcactttctg ctgcactgct atgctaatta cagtgctcgc tttggtctgt    420
accctactct atattaaata caaaaagcaga cgcagcttta ttgaggaaag cagcatgcct    480
taa                                                                   483
```

<210> SEQ ID NO 4
<211> LENGTH: 13
<212> TYPE: PRT
<213> ORGANISM: Artificial Sequence

```
<220> FEATURE:
<223> OTHER INFORMATION: Fragment of mutated carboxy-terminal fragment
      of protein E3-19K of human adenovirus type 5

<400> SEQUENCE: 4

Lys Ser Arg Arg Ser Pro Ile Glu Glu Ser Ser Met Pro
1               5                   10

<210> SEQ ID NO 5
<211> LENGTH: 2512
<212> TYPE: DNA
<213> ORGANISM: Artificial Sequence
<220> FEATURE:
<223> OTHER INFORMATION: Sequence with the regulatory regions DM1
      insulator (from position 367 to 1095); a fragment of the E2F1
      promoter (from position 1282 to 1545); the ccacc kozak sequence
      (from position 1546  to 1550); and the E1a- 24 gene (from position
      1551 to 2512)

<400> SEQUENCE: 5
catcatcaat tataccttcc attttggatt gaagccaata tgataatgag ggggtggagt      60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccatttttcgc gggaaaactg aataagagga    300
agtgaaatct gaataatttt gtgttactca tagcgcgtaa tctctagcat cgatgtcgag    360
gatccctcga gaccctgaaa ctgtcttcga ctccggggcc ccgttggaag actgagtgcc    420
cggggcacgg cacagaagcc gcgcccaccg cctgccagtt cacaaccgct ccgagcgtgg    480
gtctccgccc agctccagtc ctgtgatccg ggcccgcccc ctagcggccg gggagggagg    540
ggccgggtcc gcggccggcg aacggggctc gaagggtcct tgtagccggg aatgctgctg    600
ctgctgctgg ggggatcaca gaccatttct ttctttcggc caggctgagg ccctgacgtg    660
gatgggcaaa ctgcaggcct gggaaggcag caagccgggc cgtccgtgtt ccatcctcca    720
cgcaccccca cctatcgttg gttcgcaaag tgcaaagctt tcttgtgcat gacgccctgc    780
tctggggagc gtctggcgcg atctctgcct gcttactcgg gaaatttgct tttgccaaac    840 ccgcttttc ggggatcccg cgccccccctc ctcacttgcg ctgctctcgg agccccagcc    900
ggctccgccc gcttcggcgg tttggatatt tattgacctc gtcctccgac tcgctgacag    960
gctacaggac ccccaacaac cccaatccac gttttggatg cactgagacc ccgacattcc   1020
tcggtattta ttgtctgtcc ccacctagga cccccacccc cgaccctcgc gaataaaagg   1080
ccctccatct gcccctcgag tctagagatg ccgcaataa aatatcttta ttttcattac    1140
atctgtgtgt tggttttttg tgtgaatcga tagtactaac atacgctctc catcaaaaca   1200
aaacgaaaca aaacaaacta gcaaaatagg ctgtccccag tgcaagtgca ggtgccagaa   1260
catttctcta tcgataggta ccatccggac aaagcctgcg cgcgcccgc ccgccattg     1320 gccgtaccgc cccgcgccgc cgccccatct cgccctcgc cgccgggtcc ggcgcgttaa    1380
agccaatagg aaccgccgcc gttgttcccg tcacggccgg ggcagccaat tgtggcggcg   1440
ctcggcggct cgtggctctt cgcggcaaa aaggatttgg cgcgtaaaag tggccgggac    1500
tttgcaggca gcggcggccg ggggcggagc gggatcgagc cctcgccacc atgagacata   1560
ttatctgcca cggaggtgtt attaccgaag aaatggccgc cagtcttttg gaccagctga    1620
tcgaagaggt actggctgat aatcttccac ctccctagcca ttttgaacca cctaccttc    1680
```

-continued

| | |
|---|---|
| acgaactgta tgatttagac gtgacggccc ccgaagatcc aacgaggag gcggtttcgc | 1740 |
| agatttttcc cgactctgta atgttggcgg tgcaggaagg gattgactta ctcacttttc | 1800 |
| cgccggcgcc cggttctccg gagccgcctc acctttcccg gcagcccgag cagccggagc | 1860 |
| agagagcctt gggtccggtt tctatgccaa accttgtacc ggaggtgatc gatccaccca | 1920 |
| gtgacgacga ggatgaagag ggtgaggagt ttgtgttaga ttatgtggag cacccgggc | 1980 |
| acggttgcag gtcttgtcat tatcaccgga ggaatacggg ggacccagat attatgtgtt | 2040 |
| cgctttgcta tatgaggacc tgtggcatgt ttgtctacag taagtgaaaa ttatgggcag | 2100 |
| tgggtgatag agtggtgggt ttggtgtggt aattttttt ttaatttta cagttttgtg | 2160 |
| gtttaaagaa ttttgtattg tgatttttt aaaaggtcct gtgtctgaac ctgagcctga | 2220 |
| gcccgagcca gaaccggagc ctgcaagacc tacccgccgt cctaaaatgg cgcctgctat | 2280 |
| cctgagacgc ccgacatcac ctgtgtctag agaatgcaat agtagtacgg atagctgtga | 2340 |
| ctccggtcct tctaacacac ctcctgagat acacccggtg gtcccgctgt gcccattaa | 2400 |
| accagttgcc gtgagagttg gtgggcgtcg ccaggctgtg gaatgtatcg aggacttgct | 2460 |
| taacgagcct gggcaacctt tggacttgag ctgtaaacgc cccaggccat aa | 2512 |

<210> SEQ ID NO 6
<211> LENGTH: 1773
<212> TYPE: DNA
<213> ORGANISM: Artificial Sequence
<220> FEATURE:
<223> OTHER INFORMATION: Sequence codifying the fiber of the human adenovirus type 5 (from position 1 to 1638; and position 1666 to 1773) containing an insertion of the peptide RGD (from position 1639 to 1665) containing the RGD motif (from 1648 to 1656)

<400> SEQUENCE: 6

| | |
|---|---|
| atgaagcgcg caagaccgtc tgaagatacc ttcaaccccg tgtatccata tgacacggaa | 60 |
| accggtcctc caactgtgcc ttttcttact cctcccttg tatcccccaa tgggtttcaa | 120 |
| gagagtcccc ctggggtact ctctttgcgc ctatccgaac tctagttac ctccaatggc | 180 |
| atgcttgcgc tcaaaatggg caacggcctc tctctggacg aggccggcaa ccttacctcc | 240 |
| caaaatgtaa ccactgtgag cccacctctc aaaaaaacca agtcaaacat aaacctggaa | 300 |
| atatctgcac ccctcacagt tacctcagaa gccctaactg tggctgccgc cgcacctcta | 360 |
| atggtcgcgg caacacact caccatgcaa tcacaggccc cgctaaccgt gcacgactcc | 420 |
| aaacttagca ttgccaccca aggacccctc acagtgtcag aaggaaagct agccctgcaa | 480 |
| acatcaggcc ccctcaccac caccgatagc agtaccctta ctatcactgc ctcacccct | 540 |
| ctaactactg ccactggtag cttgggcatt gacttgaaag agcccattta tacacaaaat | 600 |
| ggaaaactag gactaaagta cggggctcct ttgcatgtaa cagacgacct aaacacttg | 660 |
| accgtagcaa ctggtccagg tgtgactatt aataatactt ccttgcaaac taaagttact | 720 |
| ggagccttgg gttttgattc acaaggcaat atgcaactta atgtagcagg aggactaagg | 780 |
| attgattctc aaaacagacg ccttatactt gatgttagtt atccgtttga tgctcaaaac | 840 |
| caactaaatc taagactagg acagggcccc ttttttataa actcagccca caacttggat | 900 |
| attaactaca acaaaggcct ttacttgttt acagcttcaa acaattccaa aaagcttgag | 960 |
| gttaacctaa gcactgccaa ggggttgatg tttgacgcta cagccatagc cattaatgca | 1020 |
| ggagatgggc ttgaatttgg ttcacctaat gcaccaaaca caaatcccct caaaacaaaa | 1080 |
| attggccatg gcctagaatt tgattcaaac aaggctatgg ttcctaaact aggaactggc | 1140 |

```
cttagttttg acagcacagg tgccattaca gtaggaaaca aaaataatga taagctaact    1200
ttgtggacca caccagctcc atctcctaac tgtagactaa atgcagagaa agatgctaaa    1260
ctcactttgg tcttaacaaa atgtggcagt caaatacttg ctacagtttc agttttggct    1320
gttaaaggca gtttggctcc aatatctgga acagttcaaa gtgctcatct tattataaga    1380
tttgacgaaa atggagtgct actaaacaat tccttcctgg acccagaata ttggaacttt    1440
agaaatggag atcttactga aggcacagcc tatacaaacg ctgttggatt tatgcctaac    1500
ctatcagctt atccaaaatc tcacggtaaa actgccaaaa gtaacattgt cagtcaagtt    1560
tacttaaacg gagacaaaac taaacctgta acactaacga tcacactaaa cggtacacag    1620
gaaacaggag acacaacttg tgactgccgc ggagactgtt tctgcccatc tgcatactct    1680
atgtcatttt catgggactg gtctggccac aactacatta atgaaatatt tgccacatcc    1740
tcttacactt tttcatacat tgcccaagaa taa                                 1773

<210> SEQ ID NO 7
<211> LENGTH: 379
<212> TYPE: DNA
<213> ORGANISM: Artificial Sequence
<220> FEATURE:
<223> OTHER INFORMATION: CMV enhancer

<400> SEQUENCE: 7
gacattgatt attgacagtt attaatagta atcaattacg ggtcattagt tcatagccc      60 atatatggag ttccgcgtta cataacttac ggtaaatggc ccgcctggct gaccgcccaa    120
cgacccccgc ccattgacgt caataatgac gtatgttccc atagtaacgc caatagggac    180
tttccattga cgtcaatggg tggactattt acggtaaact gcccacttgg cagtacatca    240
agtgtatcat atgccaagta cgccccctat tgacgtcaat gacggtaaat ggcccgcctg    300
gcattatgcc cagtacatga ccttatggga cttttcctact tggcagtaca tctacgtatt    360
agtcatcgct attaccatg                                                 379

<210> SEQ ID NO 8
<211> LENGTH: 204
<212> TYPE: DNA
<213> ORGANISM: Artificial Sequence
<220> FEATURE:
<223> OTHER INFORMATION: CMV promotor

<400> SEQUENCE: 8
gtgatgcggt tttggcagta catcaatggg cgtggatagc ggtttgactc acggggattt     60
ccaagtctcc accccattga cgtcaatggg agtttgtttt ggcaccaaaa tcaacgggac    120
tttccaaaat gtcgtaacaa ctccgcccca ttgacgcaaa tgggcggtag cgtgtacgg    180 tgggaggtct atataagcag agct                                          204

<210> SEQ ID NO 9
<211> LENGTH: 30
<212> TYPE: DNA
<213> ORGANISM: Artificial Sequence
<220> FEATURE:
<223> OTHER INFORMATION: Sequence containing I-CeuI restriction site

<400> SEQUENCE: 9
cgtaactata acggtcctaa ggtagcgaaa                                      30

<210> SEQ ID NO 10
<211> LENGTH: 1311
```

```
<212> TYPE: DNA
<213> ORGANISM: Artificial Sequence
<220> FEATURE:
<223> OTHER INFORMATION: HA tagged GSK3 beta sequence

<400> SEQUENCE: 10
atggcagggc ggcccagaac caccgccttt gcggagagct gcaagccggt gcagcagcct      60
tcagcttttg gcagcatgaa agttagcaga gacaaggacg gcagcaaggt gacaacagtg     120
gtggcaactc ctgggcaggg tccagacagg ccacaagaag tcagctatac agacactaaa     180
gtgattggaa atggatcatt tggtgtggta tatcaagcca aactttgtga ttcaggagaa     240
ctggtcgcca tcaagaaagt attgcaggac aagagattta agaatcgaga gctccagatc     300
atgagaaagc tagatcactg taacatagtc cgattgcgtt atttcttcta ctccagtggt     360
gagaagaaag atgaggtcta tcttaatctg gtgctggact atgttccgga aacagtatac     420
agagttgcca gacactatag tcgagccaaa cagacgctcc ctgtgattta tgtcaagttg     480
tatatgtatc agctgttccg aagtttagcc tatatccatt cctttggaat ctgccatcgg     540
gatattaaac cgcagaacct cttgttggat cctgatactg ctgtattaaa actctgtgac     600
tttggaagtg caaagcagct ggtccgagga gaacccaatg tttcgtatat ctgttctcgg     660
tactataggg caccagagtt gatctttgga gccactgatt atacctctag tatagatgta     720
tggtctgctg gctgtgtgtt ggctgagctg ttactaggac aaccaatatt tccaggggat     780
agtggtgtgg atcagttggt agaaataatc aaggtcctgg aactccaac aagggagcaa     840 atcagagaaa tgaacccaaa ctacacagaa tttaaattcc ctcaaattaa ggcacatcct     900
tggactaagg tcttccgacc ccgaactcca ccggaggcaa ttgcactgtg tagccgtctg     960
ctggagtata caccaactgc ccgactaaca ccactggaag cttgtgcaca ttcatttttt    1020
gatgaattac gggacccaaa tgtcaaacat ccaaatgggc gagacacacc tgcactcttc    1080
aacttcacca ctcaagaact gtcaagtaat ccacctctgg ctaccatcct tattcctcct    1140
catgctcgga ttcaagcagc tgcttcaacc cccacaaatg ccacagcagc gtcagatgct    1200
aatactggag accgtggaca gaccaataat gctgcttctg catcagcttc caactccact    1260
agctacccat acgatgttcc agattacgca agcttgggtg tcccaactaa a             1311

<210> SEQ ID NO 11
<211> LENGTH: 236
<212> TYPE: DNA
<213> ORGANISM: Artificial Sequence
<220> FEATURE:
<223> OTHER INFORMATION: polyA

<400> SEQUENCE: 11
tggatccaga catgataaga tacattgatg agtttggaca accacaact agaatgcagt        60 gaaaaaaatg ctttatttgt gaaatttgtg atgctattgc tttatttgta accattataa      120
gctgcaataa acaagttaac aacaacaatt gcattcattt tatgtttcag gttcaggggg      180
aggtgtggga ggttttttaa agcaagtaaa acctctacaa atgtgatatg gctgat          236

<210> SEQ ID NO 12
<211> LENGTH: 317
<212> TYPE: DNA
<213> ORGANISM: Artificial Sequence
<220> FEATURE:
<223> OTHER INFORMATION: SV40 promoter

<400> SEQUENCE: 12
```

```
ggtgtggaaa gtccccaggc tccccagcag gcagaagtat gcaaagcatg catctcaatt    60
agtcagcaac caggtgtgga aagtccccag gctccccagc aggcagaagt atgcaaagca   120
tgcatctcaa ttagtcagca accatagtcc cgcccctaac tccgcccatc ccgcccctaa   180
ctccgcccag ttccgcccat tctccgcccc atggctgact aatttttttt atttatgcag   240
aggccgaggc cgcctcggcc tctgagctat tccagaagta gtgaggaggc ttttttggag   300
gcctaggctt ttgcaaa                                                  317

<210> SEQ ID NO 13
<211> LENGTH: 30
<212> TYPE: DNA
<213> ORGANISM: Artificial Sequence
<220> FEATURE:
<223> OTHER INFORMATION: Sequence containing I-CeuI restriction site

<400> SEQUENCE: 13
cgtaactata acggtcctaa ggtagcgaaa                                     30

<210> SEQ ID NO 14
<211> LENGTH: 936
<212> TYPE: DNA
<213> ORGANISM: Artificial Sequence
<220> FEATURE:
<223> OTHER INFORMATION: Renilla luciferase sequence

<400> SEQUENCE: 14
atgacttcga aagtttatga tccagaacaa aggaaacgga tgataactgg tccgcagtgg    60
tgggccagat gtaaacaaat gaatgttctt gattcattta ttaattatta tgattcagaa   120
aaacatgcag aaaatgctgt tatttttta catggtaacg cggcctcttc ttatttatgg   180
cgacatgttg tgccacatat tgagccagta gcgcggtgta ttataccaga ccttattggt   240
atgggcaaat caggcaaatc tggtaatggt tcttataggt tacttgatca ttacaaatat   300
cttactgcat ggtttgaact tcttaattta ccaaagaaga tcatttttgt cggccatgat   360
tggggtgctt gtttggcatt ttattatagc tatgagcatc aagataagat caaagcaata   420
gttcacgctg aaagtgtagt agatgtgatt gaatcatggg atgaatggcc tgatattgaa   480
gaagatattg cgttgatcaa atctgaagaa ggagaaaaaa tggttttgga gaataacttc   540
ttcgtggaaa ccatgttgcc atcaaaaatc atgagaaagt tagaaccaga gaatttgca   600 gcatatcttg aaccattcaa agagaaaggt gaagttcgtc gtccaacatt atcatggcct   660
cgtgaaatcc cgttagtaaa aggtggtaaa cctgacgttg tacaaattgt taggaattat   720
aatgcttatc tacgtgcaag tgatgattta ccaaaaatgt ttattgaatc ggacccagga   780
ttcttttcca tgctattgt tgaaggtgcc aagaagtttc ctaatactga atttgtcaaa   840
gtaaaaggtc ttcatttttc gcaagaagat gcacctgatg aaatgggaaa atatatcaaa   900
tcgttcgttg agcgagttct caaaaatgaa caataa                             936

<210> SEQ ID NO 15
<211> LENGTH: 936
<212> TYPE: DNA
<213> ORGANISM: Renilla reniformis

<400> SEQUENCE: 15
atgacttcga aagtttatga tccagaacaa aggaaacgga tgataactgg tccgcagtgg    60
tgggccagat gtaaacaaat gaatgttctt gattcattta ttaattatta tgattcagaa   120
aaacatgcag aaaatgctgt tatttttta catggtaacg cggcctcttc ttatttatgg   180
```

```
cgacatgttg tgccacatat tgagccagta gcgcggtgta ttataccaga ccttattggt    240
atgggcaaat caggcaaatc tggtaatggt tcttataggt tacttgatca ttacaaatat    300
cttactgcat ggtttgaact tcttaattta ccaaagaaga tcatttttgt cggccatgat    360
tggggtgctt gtttggcatt ttattatagc tatgagcatc aagataagat caaagcaata    420
gttcacgctg aaagtgtagt agatgtgatt gaatcatggg atgaatggcc tgatattgaa    480
gaagatattg cgttgatcaa atctgaagaa ggagaaaaaa tggttttgga gaataacttc    540
ttcgtggaaa ccatgttgcc atcaaaaatc atgagaaagt tagaaccaga agaatttgca    600
gcatatcttg aaccattcaa agagaaaggt gaagttcgtc gtccaacatt atcatggcct    660
cgtgaaatcc cgttagtaaa aggtggtaaa cctgacgttg tacaaattgt taggaattat    720
aatgcttatc tacgtgcaag tgatgattta ccaaaaatgt ttattgaatc ggacccagga    780
ttcttttcca atgctattgt tgaaggtgcc aagaagtttc ctaatactga atttgtcaaa    840
gtaaaaggtc ttcatttttc gcaagaagat gcacctgatg aaatgggaaa atatatcaaa    900
tcgttcgttg agcgagttct caaaaatgaa caataa                             936
```

<210> SEQ ID NO 16
<211> LENGTH: 8
<212> TYPE: PRT
<213> ORGANISM: Artificial Sequence
<220> FEATURE:
<223> OTHER INFORMATION: part of the CR2 domain of E1A

<400> SEQUENCE: 16

Leu Thr Cys His Glu Ala Gly Phe
1               5

RECOMBINANT REPLICATION COMPETENT VIRUSES COMPRISING A CODING REGION FOR GLYCOGEN SYNTHASE KINASE-3 (GSK3) AND METHODS OF KILLING ABERRANT CELLS

RELATED APPLICATION DATA

This application is a National Stage Application under 35 U.S.C. 371 of co-pending PCT application number PCT/NL2019/050562 designating the United States and filed Aug. 30, 2019; which claims the benefit of EP application number 18192104.0.1 and filed Aug. 31, 2018 each of which are hereby incorporated by reference in their entireties.

Glycogen synthase kinase-3 (GSK3) is a multifunctional enzyme that is involved in diverse cellular processes such as cell proliferation, apoptosis, neural function, metabolism, embryonic development and insulin signaling (1, 2). There are two known isoforms of this protein; GSK3-alpha and GSK3-beta. The enzymes undergo activation or inactivation through phosphorylation in different residues. The two isoforms have similar structures but differ in cellular functions and are encoded by different genes (3).

One way of activation and inactivation of the protein occurs through the post-translational phosphorylation of tyrosine(Y) and serine (S) residues. GSK3-alpha and GSK3-beta are thought to be active in non-stimulated resting cells. Both isoforms are also able to auto-phosphorylate the Y279 residue in GSK3-alpha and the Y216 in GSK3-beta. Phosphorylation at these positions is known to increase the catalytic activity of the protein. Phosphorylation of S21 of GSK3-alpha and S9 of GSK3-beta can inactivate the respective proteins; these phosphorylated residues block a substrate binding site and can thereby inhibit GSK3 functionality (4, 5).

Deregulation of GSK3 has been linked to different diseases. Of note are some of the neuro-degenerative disorders, diabetes and cancers (1, 2). Its over-expression and its implication in tumor promoting or suppression has been reported; but may be dependent on cell type and phosphorylation status (6-8).

Over-expression of GSK3 has been described in several types of tumors, where it may act as a tumor promoter facilitating survival, cell growth and angiogenesis (9, 10). GSK3 is thought to be a cancer promoter in glioblastoma multiform, pancreatic cancer, colorectal cancer, renal cancer, leukemia and ovarian cancer (5).

Inactivation of GSK3-beta has been reported in a number of cancer types. GSK3-beta is thought to be a tumor suppressor in skin cancer, mammary cancer, oral cancer and lung cancer (5, 11-13).

One way to produce a constitutively active GSK3-beta is by substituting serine for alanine in position 9 (S9A-GSK3-beta), this prevents the formation of a phosphorylated serine at that position which can inactivate the protein. Several groups have designed small molecules to inhibit GSK3-beta activity in those cancers where GSK3 is known to be pro-tumorigenic (14-16).

Replication competent adenoviruses have attracted a renewed interest as oncolytic agents in cancer therapy in recent years. The current approaches use modifications in the adenovirus genomes that facilitate preferential viral replication in tumor cells as oppose id to normal cells. In this respect, the adenovirus mutant "ONYX-015" and the Delta24 adenovirus can serve as archetypes. The ONYX-015 virus has a deletion in the region coding for the E1B 55 kDa protein. As a result, the virus is incapable of down-regulating the p53 activity which is necessary for efficient virus replication. The Delta24 virus carries a deletion in the viral E1A gene that encompasses the region responsible for binding the RIB protein. Binding of RB is necessary for efficient replication in RB containing cells.

The present invention is the first wherein GSK3 is used to promote replication of an adenovirus and/or its oncolytic property. This is used in the present invention, for instance, for promoting the kill of infected tumor cells, and the treatment of cancer.

SUMMARY OF THE INVENTION

The invention provides a recombinant replication competent adenovirus comprising in the genome of the adenovirus a coding sequence for a glycogen synthase kinase-3 (GSK3) protein operably linked to an expression control sequence.

Also provided is a method for treating cancer in an individual comprising administering to the individual in need thereof an adenovirus of the invention.

Further provided is an adenovirus of the invention, for use in the treatment of an individual that has cancer.

Further provided is a method of killing a cancer cell comprising providing a tumor comprising said cancer cell with an adenovirus of the invention.

Also provided is a method for enhancing the rate of replication of a recombinant replication competent adenovirus in a permissive cell comprising providing the genome of said adenovirus with a coding sequence for a GSK3 protein operably linked to an expression control sequence for expressing said coding sequence in said cell.

Further provided is a method for increasing an oncolytic property of an oncolytic recombinant replication competent adenovirus comprising providing the genome of said adenovirus with coding sequence for a GSK3 protein operably linked to an expression control sequence for expressing said coding sequence.

In a further aspect is provided a method of increasing the rate of replication and spreading of a recombinant replication competent adenovirus in a tumor, the method comprising providing the oncolytic adenovirus with a coding sequence for a GSK3 protein operably linked to an expression control sequence for expressing said coding sequence in cells of said tumor.

Also provided is the use of a coding sequence for a GSK3 protein operably linked to an expression control sequence for expressing said coding sequence for enhancing the rate of replication of a recombinant adenovirus.

Further provided is a combination comprising the adenovirus of the invention with a further medicament, preferably a cancer medicament.

The invention also provides a method of treatment or, an adenovirus of the invention for use in the treatment, wherein the treatment further comprises the administration of concurrent or sequential radiotherapy, antibody therapy, chemotherapy, cell-therapy, immunotherapy or other anticancer intervention or treatment.

DETAILED DESCRIPTION OF THE INVENTION

GSK3-alpha is also known under names such as Glycogen Synthase Kinase 3 Alpha; Serine/Threonine-Protein Kinase GSK3A; GSK3 Alpha; and Glycogen Synthase Kinase-3 Alpha. A reference sequence for GSK3 alpha can be found under accessions numbers: HGNC: 4616; Entrez Gene:

2931; Ensembl: ENSG00000105723; OMIM: 606784 or UniProtKB: P49840. GSK3-beta is also known under names such as Glycogen Synthase Kinase 3 Beta; Serine/Threonine-Protein Kinase GSK3B; GSK3 Beta; Glycogen Synthase Kinase-3 Beta; and GSK3beta Isoform. A reference sequence for GSK3 beta can be found under accessions numbers: HGNC: 4617; Entrez Gene: 2932; Ensembl: ENSG00000082701; OMIM: 605004; and UniProtKB: P49841. The reference sequence is given only to identify the gene. It is not meant that the gene necessarily has exactly the same sequence as indicated in database for the respective accession codes. Natural and recombinant variants of the sequence are encompassed by the gene name.

The GSK3 protein encoded by an adenovirus as described herein is preferably a GSK3-beta protein. The GSK3 protein is preferably a mutant protein that is constitutively active. In that respect the GSK3 protein is preferably a GSK3-beta protein wherein the serine residue at position 9 is substituted by another amino acid residue, preferably an alanine residue.

A coding sequence for GSK3 typically comprises a cDNA of the gene. A cDNA is typically shorter than a genomic sequence and shorter sequences are preferred in a recombinant virus. On the other hand, expression in a cell is typically enhanced by the presence of one or more introns. Such an intron may be a natural intron of the GSK3 gene. Preferably the intron is an artificial intron, preferably introduced in the 5'-non coding region of the pre-mRNA that comprises the coding region.

The coding region is preferably operably linked to an expression control sequence such as a promoter. A promoter is typically linked to an enhancer sequence. A combination of a promoter and an enhancer is sometimes collectively referred to as a promoter. The promoter is a promoter that is active in a tumor cell. Preferred promoters are the CMV promoter, the SV40 promoter, or a house keeping gene promoter such as the PGK promoter. The expression control sequence can also be an endogenous viral promoter, e.g. the endogenous major late promoter (MLP) of adenovirus serotype 5. In this case, the coding sequence can be operably linked to the MLP e.g. via alternative splicing to an inserted splice-acceptor site analogous to that of the adenovirus serotype 40 long fiber gene (Carette et al., J Gene Med. 2005 August; 7(8):1053-62).

The invention provides a recombinant virus comprising a nucleic acid molecule comprising a GSK3-beta coding region operably linked to a promoter. The recombinant virus is preferably an adenovirus (Ad), herpes simplex virus (HSV), vaccinia virus, poliovirus, reovirus, vesicular stomatitis virus (VSV), semliki forest virus, senecavirus, or a maraba virus. The virus is preferably a replication competent virus. A replication competent virus, such as a recombinant replication competent adenovirus as described herein can replicate in and lyse a cancer cell. Replication competent in the context of the present invention refers to a virus that possesses all the necessary machinery to replicate in a permisive cell. Replication competence is further exemplified using adenovirus as an example. The same principle applies to other viruses. The replication competent adenovirus does not need the assistance of an additional adenovirus protein in a packaging cell. For instance an E1-deleted replication defective adenovirus requires a complementing cell that provides the E1 proteins in trans for efficient replication. Many replication competent adenoviruses replicate more efficiently in cancer cells than in normal cells. Interest in such viruses was increased with the first recombinant adenoviruses that were modified to enhance the preferential replication in cancer cells. The modification comprises a modification of the virus genome such that one or more parts that are necessary for efficient replication of the adenovirus in normal cells but not in cancer cells have been modified, removed or have otherwise been engineered to be not expressed in normal cells. Adenoviruses that preferentially replicate in cancer cells are also called "oncolytic adenoviruses". Oncolytic adeno virus as employed herein means an adenovirus that preferentially kills cancer cells as compared to non-cancer cells. In a preferred embodiment the replication competent adenovirus as described herein comprises a modification in the virus genome that enables preferential replication of the adenovirus in tumor cells. The modification is preferably a mutation in of the virus genome. The mutation is preferably in the E1A region, the E1B region, the E4-region or a combination of one or more thereof. Many oncolytic adenoviruses comprise a mutation in one or more these regions. An adenovirus according to the invention preferably carries a mutation in the E1A region, preferably encompassing at least a part of the CR2 domain of E1A, preferably a deletion encompassing amino acids 122 to 129 (LTCHEAGF) of E1A. Such a deletion is referred to as the delta-24 deletion. An example of an E1A with the indicated E1a-Δ24 mutation is indicated from position 1551 to 2512 of SEQ ID NO:5. The term gene or region, as used herein, comprises the complete genomic region that is required for expression of a gene including, for example, an enhancer region, a promoter region and intronic en exonic sequences. Another mutation that enables preferential replication in tumor cells is the elimination of the protein E1b-55K or at least the expression thereof. E1b-55K inactivates p53 to induce in the infected cell the entry in phase S of the cell cycle and to prevent cell apoptosis. An adenovirus mutated in E1b-55K is known as Onyx-015. This virus has been used to treat tumors that are defective in p53. Adenoviruses with the earlier mentioned delta-24 mutation achieve selective replication in tumors in a different way. The delta-24 mutation affects the conserved region 2 (CR2) of E1a. This E1a region mediates binding to proteins of the Retinoblastoma (Rb) family. pRb proteins block the transition of the Go/G1 phase to the S phase of the cell cycle, forming a complex transcription inhibitor along with E2F. When E1a binds to a pRb, the E2F transcription factor of the pRb-E2F complex is released and E2F acts as a transcriptional activator of genes responsible for moving on to the S phase and viral genes such as E2. The release of E2F is thus a key step in the replication of the adenovirus. In tumor cells, the cell cycle is out of control because pRb is absent or inactivated by hyperphosphorylation and E2F is free. In these cells, the inactivation of pRb by E1a is now not necessary. Thus, an adenovirus with a mutation in CR2 propagates in cells wherein E2F is free such as many cancer cells and replicates much less efficiently in normal cells with a functional pRb.

Preferential replication can also be achieved by replacing a viral promoter with a tumor-selective promoter. In this embodiment the modification comprises a promoter of tissue or cell type specific expression of E1A or E1B. An example is a modification wherein the E1a promoter has been replaced another promoter. Various promoters have been used to this effect, such as the alpha-fetoprotein promoter, a prostatic-specific antigen (PSA) promoter, a kallikrein promoter, a mucine 1 promoter or an osteocalcin promoter. Such adenoviruses replicate more efficiently in (particular) tumor cells but, as a result of incomplete shut-off of the replacement promoter also some replication in normal cells. Nowadays recombinant adenoviruses exist wherein more than one early region promoter have been replaced by a tumor cells selective promoter. The regulation of various viral genes can be done with a different promoter for each viral gene, for example the E2F1 promoter for E1a and the telomerase promoter for E4. In this case, the two promoters must be expressed at suitable levels to allow viral replication such that oncolytic potency remains in many tumor cells. Alternatively, two viral genes can be regulated by the same promoter, for example in the oncolytic adenovirus Onyx 411, in which E1a and E4 are regulated by the E2F1 promoter.

In some embodiments preferential replication is achieved by replacing a viral promoter of a for replication essential viral gene with a tumor-selective promoter. Specific embodiments of the invention include oncolytic adenoviral vectors whose replication is restricted to cells with a deregulated p16/Rb pathway by selectivity expressing an adenovirus E1 protein, preferably an E1A protein, by replacing all or part of the E1A promoter with an E2F (e.g. E2F1) responsive promoter. In a preferred embodiment the E1A gene is operably linked to an E2F1 promoter. Preferential replication can also be achieved by a combining one or more different means for achieving selectivity. A preferred combination is an E2F1 promoter regulating the E1A gene with a delta-24 mutation (Majem et al., Cancer Gene Ther. 2006 July; 13(7):696-705 and Alonso et al., Cancer Res. 2007 Sep. 1; 67(17):8255-63).

In another aspect the modification comprises a mutation of a nucleic acid sequence in the E3-region or a deletion of the entire E3-region. Mutations in the E3-region can enhance the oncolytic effect of a replication competent adenovirus. One such mutation is a mutation in the endoplasmic reticulum retention domain of E3-19K. The E3-19K protein is known to regulate the presence of MHC-I on the cell membrane. One function of the protein relates to the binding to MHC-I and another function relates to the retention of E3-19 protein and MHC-I bound thereto in the endoplasmic reticulum. Expression of E3-19k in a cell prevents the transit of MHC-I to the plasma membrane and the presentation of antigens associated to MHC-I. Expression of E3-19K is thus associated with a reduced immune response to adenovirus infected cells. On the other hand, it was found that a mutation in E3-19K that prevents it's retention in the endoplasmic reticulum can increase the oncolytic potential of the adenovirus. In one embodiment an adenovirus of the invention comprises a modified E3-region. The modification can be a deletion of one or more parts or the whole of the E3-region. In one embodiment the modification comprises a mutation in the E3-19K protein that prevents the retention of E3-19K in the endoplasmic reticulum. In particular, the carboxy-terminal domain of E3-19K is eliminated or modified to prevent the retention of E3-19K in the endoplasmic reticulum and to cause its transit to the plasma membrane. An adenovirus that replicates and that contains this particular mutation of E3-19K is released more efficiently from the infected cell. This higher release causes a higher oncolytic effect. This enhanced oncolytic effect is useful to treat cancer. A preferred mutation in E3-19K is described in WO2008/110579 which is incorporated by reference herein. The suitable E3-mutations are described and exemplified therein by SEQ ID NOs: 1, 2, 4 and 5. The sequences are reiterated herein as SEQ ID NOs: 1, 2, 3, and 4. The replicative adenovirus of the invention preferably expresses an E3-19K with a carboxy-terminus tail having a SEQ ID NO 4. In another embodiment of the invention, the replicative adenovirus comprises at least the nucleotide sequences SEQ ID NO:1, SEQ ID NO: 5 and SEQ ID NO: 6. The replicative adenovirus of the present invention in one embodiment expresses an E3-19K with a carboxy-terminus tail having a SEQ ID NO: 2; and has an insertion of the RGD motif in the fiber protein (defined from position 1648 to 1656 of SEQ ID NO:6); and regulatory regions conferring selective replication of said adenovirus in tumor cells, said regulatory regions consisting in DM1 insulator (defined from position 367 to 1095 of SEQ ID NO: 5), a fragment of the E2F1 promoter (defined from position 1282 to 1545 of SEQ ID NO: 5), the ccacc kozak sequence (defined from position 1546 to 1550 of SEQ ID NO: 5) and the adenovirus E1a-Δ24 mutant gene (defined from position 1551 to 2512 of SEQ ID NO:5). Another object of the invention is a replicative adenovirus comprising a mutation in the endoplasmic reticulum retention domain of E3-19K which prevents the retention of E3-19K in the endoplasmic reticulum, wherein said adenovirus comprises the nucleotide sequence SEQ ID NO: 1. In another aspect of the invention, the replicative adenovirus expresses an E3-19K with a carboxy-terminus tail having a SEQ ID NO:2. In one embodiment the replicative adenovirus is ORCA-10 as described in Dong, W et al. (2014, Human Gene Therapy 25: 897-904). The GSK3beta coding region is preferably inserted as a cDNA as indicated in FIG. 5 or FIG. 6. The GSK3beta is preferably a constitutively active GSK3beta. The constitutively active GSK3beta is preferably a GSK3beta wherein the serine residue at position 9 is replaced by another amino acid residue. The GSK3beta mutant is preferably an S9A mutant, where S is a serine and A is alanine.

An adenovirus according to the invention may comprise a modification that increases its replication potential, such as e.g. retention of the E3 region (Suzuki et al., Clin. Cancer Res. 8(2002):3348-3359) or deletion of the E1B-19K gene (Sauthoff et al. Hum. Gene Ther. 11(2000):379-388), or that increase the replication selectivity for a certain type of cells, including but not limited to the modifications to facilitate selective expression of an early region gene in cancer cells, or that reduce or enhance the immunogenicity (i.e., their potency to induce an immune response when introduced into an animal body), such as e.g. retention of the E1B region (Wang et al., Nature Biotechnol. 21(2003):1328-1335).

Tumor therapies are based on medicaments and treatments that selectively kill tumor cells. Such treatments aim to spare normal 'healthy' cells as much as possible. The tumor cell can die as a result of the cytopathic effect caused by among others the internal replication of the virus, as a result of the expression of an additionally introduced gene, an immune response towards the tumor cell and/or other causes (such as but not limited to additional toxin(s) associated with the virus. Lysis of the tumor is called oncolysis. Adenoviruses that replicate selectively in tumors are called oncolytic adenoviruses. An oncolytic adenovirus is a replication-competent adenovirus that has been developed to preferentially replicate in cancer cells. Replication is preferential for a cancer cell when the virus replicates 20%, preferably 30%, 40%, 50%, 80% more preferably 100% faster in said cancer cells than in healthy cells derived from the same cell type as the cancer cell originated from.

The invention further provides a method for treating cancer in an individual comprising administering to the individual in need thereof a recombinant replication competent adenovirus comprising in the genome of the adenovirus a coding sequence for a glycogen synthase kinase-3 (GSK3) protein operably linked to an expression control sequence.

The term cancer refers to malignant primary and/or metastasized cancers. Examples of a cancer include, but are not limited to, a carcinoma; a sarcoma, a lymphoma, a leukemia, a melanoma, or a myeloma. The cancer is preferably bone cancer, brain cancer, eye cancer, breast cancer, skin cancer such as melanoma, head and neck squamous carcinoma (HNSCC), bladder cancer, lung cancer, ureter cancer, urethra cancer, thyroid cancer, parathyroid cancer, salivary gland cancer, kidney cancer, prostate cancer, genital system cancer including cervix cancer, ovary cancer and testis cancer, endometrium cancer, blood/hematologic system cancer, or in a gastrointestinal tissue cancer such as colon cancer. In a preferred embodiment said cancer is a prostate cancer, a skin cancer, a lung cancer or a pancreatic cancer. A host cell is preferably a cancer cell. The cancer cell is preferably a malignant primary and/or metastasized cancer cell. A cancer cell can be a carcinoma cell; a sarcoma cell, a lymphoma cell, a leukemia cell, a melanoma cell or a myeloma cell. A cancer cell can also be a bone cancer cell, brain cancer cell, eye cancer cell, breast cancer cell, skin cancer cell such as a melanoma cell or a HNSCC cell, bladder cancer cell, lung cancer cell, ureter cancer cell, urethra cancer cell, thyroid cancer cell, parathyroid cancer cell, salivary gland cancer cell, kidney cancer cell, prostate cancer cell, genital system cancer cell including ovary cancer cell and testis cancer cell, endometrium cancer cell, blood/hematologic system cancer cell, or in a gastrointestinal tissue cancer cell. A tumor typically comprises the cancerous cell and supporting cells such as stroma cells, vascular cells, blood and/or immune cells. The term cancer cell refers to the cancerous cell and not to a supporting cell. The replication competent adenovirus may also infect and replicate in a supporting cell. The words tumor and cancer are used interchangeably herein.

The cancer cell is preferably a cancer cell that does not express, or does not over express GSK3. The GSK3 that is not expressed or not over-expressed is preferably GSK3 beta.

It is preferred that the GSK-coding region in the adenovirus of the invention comprises a constitutively active GSK3. The constitutively active GSK3 is preferably a mutant with an activating mutation at position S21 in GSK3 alpha, or position S9 in GSK3 beta. The activating mutation is preferably a replacement of the codon for serine residue (at position 21 or 9 respectively) by a codon for an alanine residue at the indicated position.

The invention also provides a method for enhancing the rate of replication of a recombinant replication competent adenovirus in a permissive cell comprising providing the genome of said adenovirus with a coding sequence for a GSK3 protein operably linked to an expression control sequence for expressing said coding sequence in said cell. A measure for the replication rate is the time it takes for a adenovirus infected cell to exhibit a cytopathic effect (CPE). The replication rate can also be measured by measuring the number of infectious particles that are produced at a certain time after infection. Replication rate is typically assessed relative to another adenovirus. When two different viruses are tested in parallel under otherwise identical circumstances the virus that shows the quickest increase in the number of infectious virus particles produced or the quickest induction of CPE has the higher replication rate. A cell is a permissive cell if it supports the replication of the replication competent adenovirus as described herein.

The invention also provides a method for increasing an oncolytic property of an oncolytic recombinant replication competent adenovirus comprising providing the genome of said adenovirus with coding sequence for a GSK3 protein operably linked to an expression control sequence for expressing said coding sequence.

The invention further provides a method of increasing the rate replication and spreading of a recombinant replication competent adenovirus in a tumor, the method comprising providing the oncolytic adenovirus with a coding sequence for a GSK3 protein operably linked to an expression control sequence for expressing said coding sequence in cells of said tumor.

An adenovirus as described herein can have one or more coding regions for further transgenes. Examples of a suitable further transgenes are IL2, GM-CSF, and TNF-alfa.

Other suitable transgenes are described elsewhere herein.

Human adenoviruses can presently be subdivided in seven species (A to G) and 57 different (sero)types.

The different serotypes are presently classified as follows:
Species A: serotypes 12, 18, 31;
Species B: serotypes 3, 7, 11, 14, 16, 21, 34, 35, 50, 55;
Species C: serotypes 1, 2, 5, 6, 57;
Species D: serotypes 8-10, 13, 15, 17, 19, 20, 22-30, 32, 33, 36-39, 42-49, 51, 53, 54, 56;
Species E: serotype 4;
Species F: serotypes 40, 4i; and
Species G: serotype 52

The adenovirus of the invention is preferably a B, C or D adenovirus. Preferably a B or a C adenovirus. The adenovirus is preferably a species C adenovirus. The adenovirus is preferably a serotype 1, 2, 3, 4, 5, 6, 7, 8, 9, 10, 11, 13, 14, 15, 1, 17, 19, 20, 21, 22-30, 32, 33, 31, 35, 36-39, 42-19, 50, 51, 53, 54, 56 or 57 adenovirus. In a preferred embodiment the adenovirus is a 1, 2, 3, 5, 6, 7, 11, 14, 16, 21, 34, 35, 50, 55, or 57 adenovirus. The adenovirus is preferably a 1, 2, 5, 6 or 57 adenovirus, preferably a 2 or 5 adenovirus. It is not very difficult to produce chimeric adenoviruses that contain a part from one adenovirus serotype and another part form another serotype, Chimeric adenoviruses that contain parts of serotypes of the same species are known. For instance chimeric serotype 2 and 5 viruses. Chimeric viruses that contain early genes of one serotype and late genes of another are also contemplated. Adenoviruses that contain chimeric adenovirus proteins are also known. For instance chimeric adenovirus fiber proteins wherein the fiber shaft and knob domains of a adenovirus virus were genetically replaced with the corresponding domains from adenovirus-3 adenovirus-11, or adenovirus-35 are described in Murakami et al 2010, Prostate Vol 70(4):pp 362-376). These particular chimeric adenoviruses have a modified target cell tropism when compared to adenovirus 5.

Said adenovirus is preferably an adenovirus serotype 5, an adenovirus serotype 24 an adenovirus serotype 35, or an adenovirus serotype 51 based virus, or a chimeric adenovirus, for example based on a serotype 5 with serotype 35 tropism by replacing a part of the serotype 5 fiber with a part of the fiber of serotype 35. Said adenovirus may further provide expression of a therapeutic transgene such as, preferably, p53, a tumor antigen, or a secreted protein such as a growth factor, cytokine or chemokine. Said adenovirus is replication competent, in particular oncolytic. Said adenovirus is a human or primate adenovirus for infection of, and replication in, human and primate cells. Said adenovirus is another mammalian adenovirus, for example a canine or equine adenovirus for infection of, and replication in, dog cells or horse cells, respectively.

A preferred adenovirus according to the invention is a human adenovirus, preferably of serotype 5.

Replication competent adenoviruses can replicate in many different cells in an animal body, provided that they are derived from adenoviruses with the correct species tropism and that said cells express surface receptors for said adenoviruses. Specific cell surface recognition by recombinant adenoviruses including replication competent adenoviruses can be changed by pseudotyping or targeting, as is known to the skilled person.

The invention further provides an adenovirus according to the invention for use as a medicament. The invention further provides an adenovirus according to the invention for use as a medicament for the treatment of cancer. Adenoviruses are propagated according to standard methods in the fields of adenovirology and adenoviral vectors. The preferred method of propagation is by infecting a suitable cell line that allows replication of adenoviruses. An example of a method for generating adenoviruses may further comprise the steps of collecting the cells when they show cytopathic effect, indicative of virus production and freeze-thawing of the cells to generate a cellular extract. The virus can be purified from the cellular extract using standard techniques, e.g. banding on a cesium chloride gradient and dialysis, for example against Phosphate-Buffered Saline-10% glycerol. An alternative for CsCl is the Vivapure virus purification kit (Sartorius). Dialyzed and/or purified virus may be aliquoted and stored at −80° C. The quantification of the number of plaque-forming adenovirus particles and units is performed according to standard protocol. A saline phosphate buffer with 10% glycerol is a standard formulation for the storage of adenovirus.

The adenovirus can be administered to an animal or human body to infect cells in vivo. Administration can be done via several routes including, but not limited to, locoregional injection into the tumor or into a body cavity where the tumor is located, injection into the blood circulation, inhalation and application to the surface of a certain body area. Following infection, the replication competent adenovirus can replicate and spread to other cells, provided that the infected cells support replication of said recombinant adenovirus. The replication competent adenovirus can thus be used to re-infect new cells to further propagate and expand said replication competent adenovirus.

The adenovirus preferably is formulated into an aqueous or solution medium for the preservation of viral particles which can directly be administered to an organism. The formulation preferably comprises pharmaceutical acceptable salts and excipients such as, for example, human serum albumin, sugars such as sucrose and mannitol, and/or a surfactant such as, for example, a difunctional block copolymer surfactant terminating in primary hydroxyl groups (Pluronic F68™).

In one embodiment, a replication competent adenovirus according to the invention may further comprise one or more expression cassettes that mediates expression of one or more small or non-protein coding RNA molecules such as miRNAs or shRNAs. A small or non-protein coding RNA molecule can be specific for a p53 antagonist and/or inhibitor of the p53 pathway or a combination thereof in a cell.

Previously, we found that oncolysis and release of adenovirus progeny from infected cancer cells can be accelerated by restoring p53 functions in said cancer cells (van Beusechem et al., Cancer Res. 62(2002):6165-6171; WO 03/057892, incorporated by reference herein). Said restoring of p53 functions is done by expressing in said cancer cells a restoring factor, i.e. a functional factor of the p53-dependent apoptosis pathway, the function whereof is not or insufficiently expressed in said cancer cells, wherein said restoring factor preferably comprises a protein (WO 03/057892). Hence, said restoring factor is an essential positive component of the p53-dependent apoptosis pathway.

A loss of normal function of p53 is associated with resistance to programmed cell death, cell transformation in vitro and development of cancers in vivo. In approximately 50% of human cancers the gene encoding p53 is non-functional through deletion or mutation (Levine et al, Nature 351(1991):453-456; Hollstein et al, Science 253(1991):49-53; Chang et al, J. Clin. Oncol. 13(1995):1009-1022). In many of the other 50% cancer cells that do express wild-type p53 protein, p53 function is still hampered by the action of a p53 antagonist. An example of a p53 antagonist is MDM2. Loss of the tumor-suppressor protein p14ARF or overexpression of MDM2 protein can lead to functional inactivation of p53 by binding to the MDM2 protein and subsequent degradation. In addition, even if p53 function itself is intact, p53-dependent cell death can be hampered due to overexpression of anti-apoptotic proteins acting on the p53 pathway down-stream from p53, such as the anti-apoptotic bcl-2 and IAP family members and BI-1. Another example is p73DeltaN, which binds to p53-responsive promoters competing with p53, thereby antagonizing p53-dependent cell death (Kartasheva et al, Oncogene 21(2002):4715-4727). The expression of one or more RNAi-mediating molecules that are specific for one or more p53 antagonists and/or inhibitors of the p53 pathway or a combination thereof in a cell will enhance the lysogenic activity in a target cell that comprises functional p53.

Said antagonists and/or inhibitors of the p53 pathway are preferably selected from synoviolin, MDM2, Pirh2, COP1, Bruce, HPV-E6, herpesvirus-8 LANA, Parc, Mortalin, Plk-1, BI-1, p73DeltaN, bcl-2, bcl-xL, bcl-w, bfl-1, brag-1, mcl-1, cIAPi, cIAP2, cIAP3, XIAP and survivin. The expression cassette further comprises one or more expression control sequences, functional in the said host cells such as an enhancer/promoter and a terminator that are operably linked to the one or more RNAi-mediating molecules. As an alternative, the expression of the one or more p53 antagonists and/or inhibitors of the p53 pathway or a combination thereof is operably linked to the control elements that mediate expression of the at least one DNA sequence coding for a silencing factor functional in reducing expression of a target gene in the host cells. It has been found that a cancer cell can contain more than one p53 antagonists and/or inhibitors of the p53 pathway. Such cells are more effectively lysed when they are provided by RNAi against at least two of those p53 antagonists and/or inhibitors of the p53 pathway.

In a further embodiment, a replication competent adenovirus according to the invention further comprises a DNA sequence that encodes at least one restoring factor functional in restoring the p53 dependent apoptosis pathway in the host cells, operably linked to one or more expression control elements, functional in the host cells. Said restoring factor preferably is selected from the pro-apoptotic death genes of the bcl-2 family, such as bax, bak, bad, bid, bik, bim, bok, blk, hrk, puma, noxa and bcl-xS (Miysitar and Reed, Cell 80(1995):293-299; Han et al Genes Dev, 1010996):461-477; Zoernig et al., Biochim. Biophys, Acta 1551(2001):F1-F37) ad/or p53, or a functional part or derivative thereof, A preferred restoring factor functional in restoring the p53 dependent apoptosis pathway is p53.

The replication competent adenovirus may further comprise a DNA sequence coding for a silencing factor functional in reducing expression and/or activity of POT1 in the cancer cell. The silencing factor is preferably an anti-sense RNA such as an RNAi or a splice modulating oligonucleotide. The artisan is well capable of designing suitable RNA based silencing factors for reducing expression of POT1 in the cancer cell. In case of POT1 it is preferred that the cancer and/or cancer cell is prostate cancer. It is further preferred that the treatment of the prostate cancer further comprises irradiating said cancer.

Viral vectors are replication deficient and require a packaging cell to provide a complementary genre to allow replication.

Adenovirus genome as employed herein means the DNA sequence encoding the structural proteins and elements relevant to the function/life cycle of an adenovirus.

A replication competent adenovirus, as defined herein, is an adenovirus that comprises, as part of its genome, the function to be replicated in the host cell, wherein replication is dependent on the replication functions provided by the virus, in combination with the endogenous cellular machinery of the host cells. The genome of the host cells does therefore not need to have exogenous sequences encoding factors that are necessary for viral replication. The term "endogenous" means in this respect that the cellular machinery (including the coding sequences therefore), necessary for virus replication, is the naturally present machinery, e.g. not introduced in the cells by manipulation techniques by man. The latter are defined as "exogenous". Replication functions, as defined, are factors such as proteins, encoded by the virus, necessary for replication of the virus in the host cells and are herein also referred to as viral replication factors.

It is important to note that these factors are encoded by the viral genome and need not be complemented by exogenous factors. Thus, viruses, of which the replication is dependent on one or more replication functions, being deleted from the virus, but introduced in the host cell, are defined to be replication deficient, and are therefore not part of the present invention. The invention as claimed relates to replication competent viruses, i.e. wherein the viral genes encoding viral replication factors, essential for regulation of virus replication in the host cells are present on the viral genome. The host cell is typically a cancer cell, or a cancer like cell.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 1. GSK3-beta expressing adenovirus inhibits the growth of human cancer cells in vitro, but not primary non-malignant human cells in vitro. FIG. 1C. Pictures of primary fibroblasts on day 6 after infection with ad.LUC or ad.CA.GSK3-beta.

FIG. 2. Induction of cell apoptosis in different melanoma cell lines by transduction with ad.CA.GSK3-beta.

FIG. 3. GSK3-beta expressing adenovirus induces selectively cancer cell killing in primary melanoma tumor suspensions.

FIG. 4. Expression of GSK3-beta enhances adenoviral replication.

FIG. 4A shows uninfected 911 cells and their growing kinetics, reaching confluency at day 3. FIG. 4B displays the 911 cells infected with ad.LUC at 1 MOI which had full cytopathogenic effect (CPE) at day 3 and a half (84 hours post infection). GSK3-beta expressing adenovirus (ad.CA-GSK3-beta) had full CPE on day 1 post infection (FIG. 4C).

EXAMPLES

In the figures and the examples different names are used to indicate the same virus. The adenovirus that has the GSK3-beta S9A coding region is referred to as adGSK3b; ad.CA.GSK3-beta; Ad.CA.GSK3-beta; and ad.CA.GSK3-beta S9A etc. The adenovirus that has the reference luciferase coding region is referred to as ad.LUC; Ad.LUC and Ad.Luc etc.

Example 1 GSK3-Beta Expressing Adenovirus Inhibits the Growth of Human Cancer Cells, but not Primary Non-Malignant Human Cells, In Vitro To evaluate the effect of GSK3-beta expressing adenovirus on cancer cells and non-malignant cells, we cultured 4 different melanoma cell lines (SK-MEL-28, JUSO, MEL57 and WM9) and a skin-derived primary fibroblasts (Fibro) freshly isolated from healthy skin.

Cells were cultured in complete RPMI medium (RPMI HEPES and L-Glutamine medium (Lonza) supplemented with 10% heat-inactivated FCS (HyClone), 100 IU/mL sodium-penicillin, 100 ug/mL streptomycin, 2 mM L-glutamine and 50 uM β-mercaptoethanol). Cells (SK-MEL-28, JUSO, MEL57, WM9 or Fibro) were seeded in a 96 well plate (10000 cells per well). 24 hours post plating cells were infected either with 500 multiplicity of infection (MOI) Ad.LUC (Ad5Luc1, (ref 17) Krasnykh et al. J. of Virology, 75 (2001):4176-4183) or Ad.CA.GSK3-beta (Kim et al. (ref 18) J. of Bio. Chemistry, 277 (2002): 41888-41896). Cells were incubated at 37° C. and 5% CO2 in the IncuCyte Zoom (EssenBioscience) and followed for 8 days in culture. Pictures of the wells were taken every 4 hours by the IncuCyte zoom. IncuCyte Zoom Software was used to analyze the wells, a confluence mask was applied by the software to obtain the percentage of confluence per well at the different time points of measurement. Confluency data was plotted on a graph using Graphpad Prism (Graphpad).

Infectious titer of viruses was determined by titration of the viruses on 911 cells using the Adeno-X rapid titration kit (BD Clontech). 500 MOI refers to 500 infectious viral particles per cell as determined by virus titration using the Adeno-X rapid titration kit.

Figure 1A:
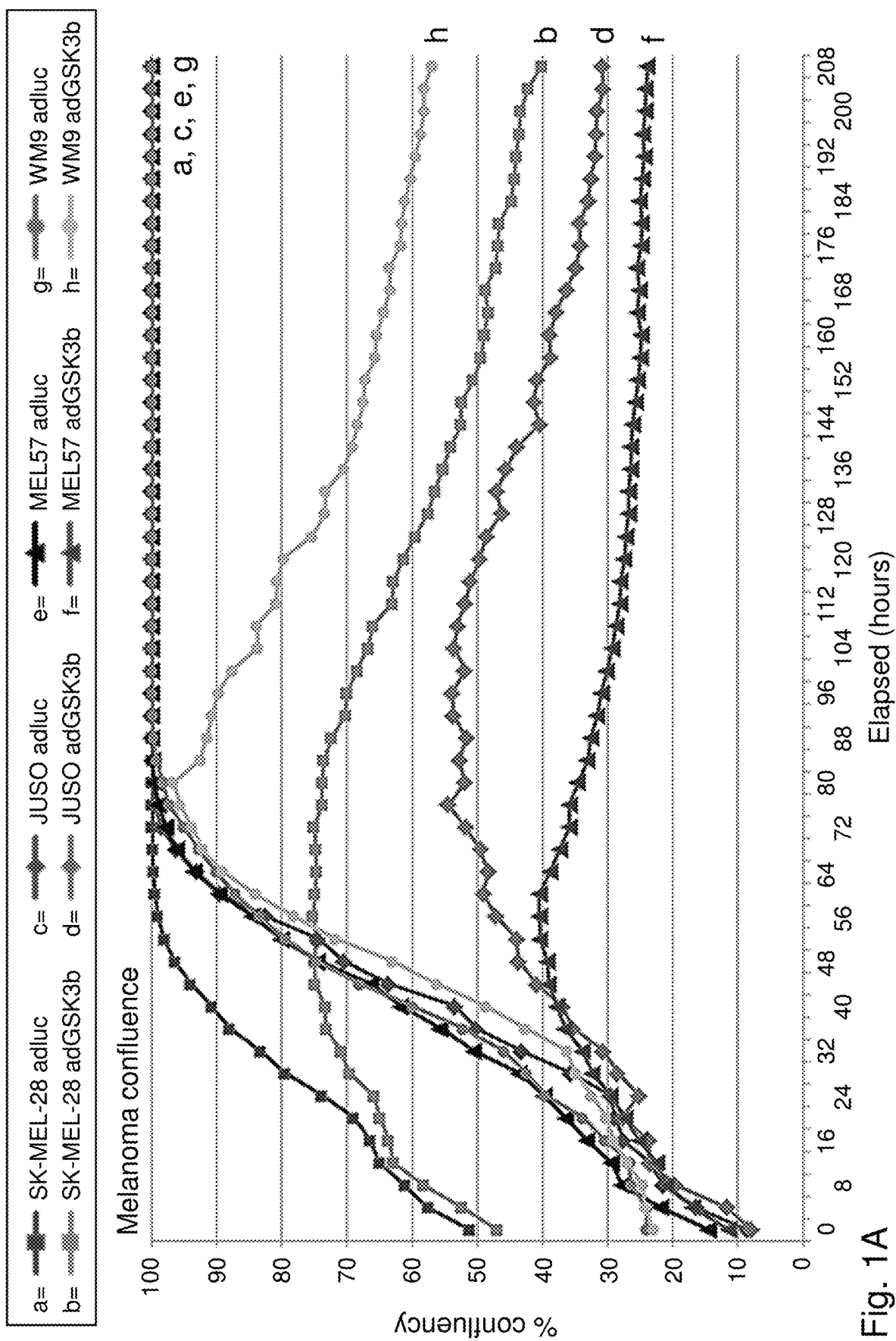
FIG. 1A GSK3-beta expressing adenovirus inhibits cancer cell proliferation in vitro. GSK3-beta expressing adenovirus (adGSK3b) inhibits growth of 4 melanoma cell lines (SK-MEL-28, JUSO, MEL57 and WM9). As control a luciferase expressing adenovirus (adLuc) was used. Cells were infected and followed for 8 days in culture; pictures of the wells were taken every 4 hours by IncuCyte.
Figure 1B:
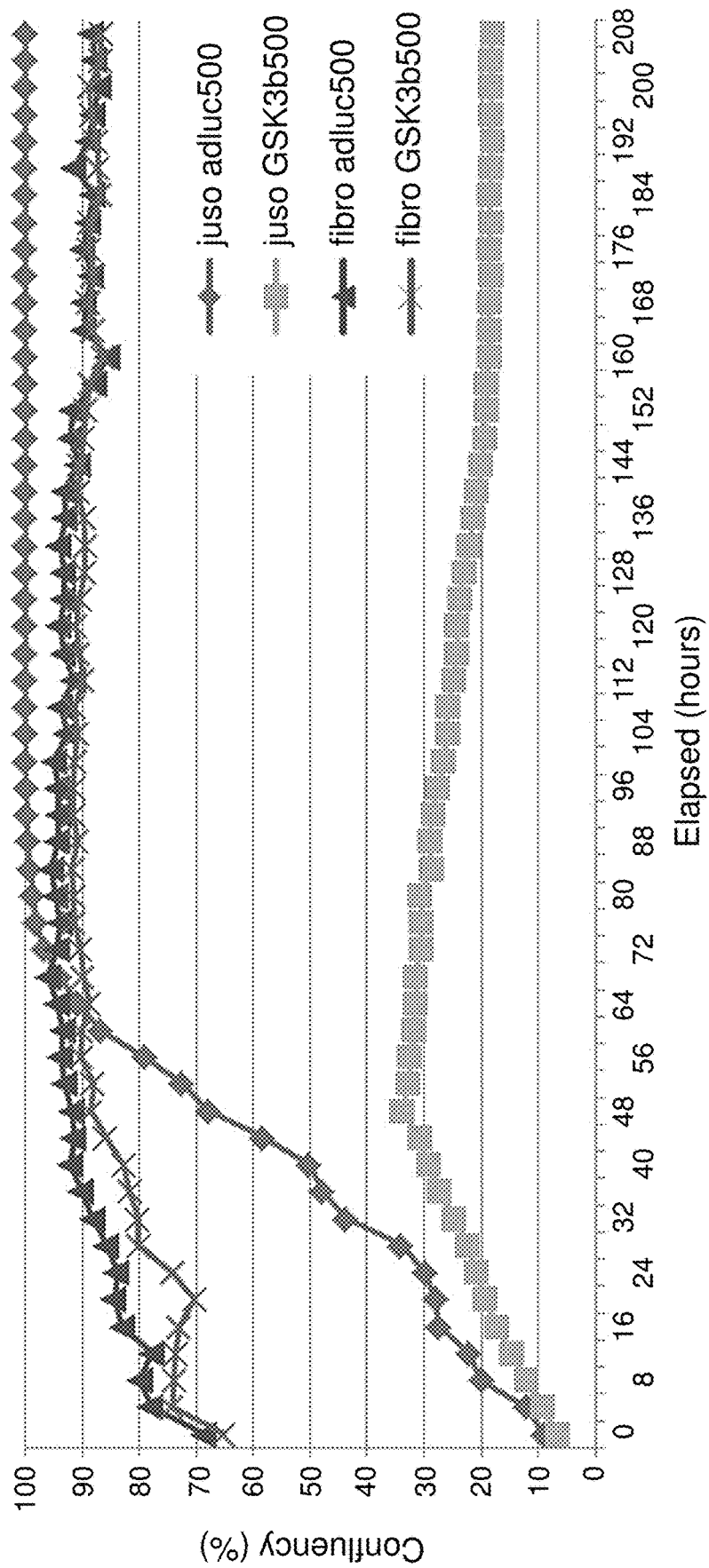
FIG. 1B GSK3-beta expression does not affect growth of normal primary fibroblasts. GSK3-beta expressing adenovirus does not inhibit growth of non-transformed primary human fibroblasts. As control the cancer cell line JUSO was taken along, which is growth inhibited.

The results demonstrated that the cancer cells infected with the GSK3-beta-expressing virus are growth inhibited and that the number of cells start to decrease after 3 to 4 days post infection, indicating cell death (FIG. 1A). In contrast, viruses expressing luciferase do not inhibit growth of the cancer cells and the wells become confluent at approximately 4 days. As demonstrated in FIGS. 1B and 1C, this is a specific anti-cancer effect, as primary human fibroblasts are not growth inhibited by infection with Ad.CA.GSK3-beta.

Taken together, these data demonstrate that the adenoviral enforced expression of a constitutively active form of GSK-beta kills cancer cells while it doesn't show any impact on primary fibroblasts.

Example 2. Induction of Apoptosis in Human Melanoma Cell Lines by Transduction with Ad.CA.GSK3-beta To demonstrate that ad.CA.GSK3-beta was able to induce cancer cell killing, 10.000 melanoma cells (SK-MEL-28, JUSO, Mel57 or WM9) were plated in a 96 well plate in complete RPMI medium. 24 hours post plating the cells were infected with 500 MOI of Ad.LUC or Ad.CA.GSK3-beta together with a 1:1000 FITC Caspase3/7 reagent (IncuCyte) following the manufacturer's procedure. Cells were incubated for 8 days at 37° C. and 5% CO2 in the IncuCyte Zoom. Pictures of the wells were taken every 4 hours by IncuCyte. IncuCyte Zoom Software was used to analyze the data, a confluence and a green confluence mask were applied by the software to obtain the percentage of confluence per well and the percentage of green signal in the well respectively. The fraction apoptotic cells was determined by dividing the green mask value by the confluence value at the different time points.

Figure 2A:
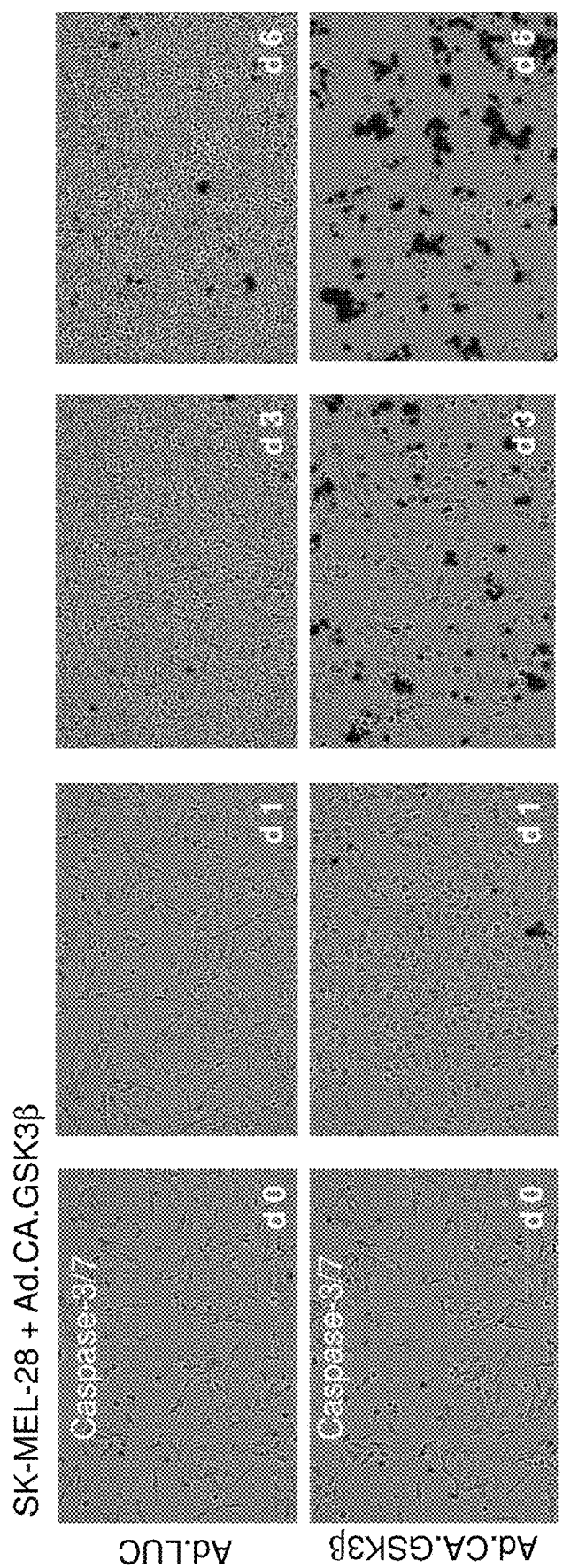
FIG. 2A Cancer cells infected with Ad.CA.GSK3-beta are visibly affected on day 1, with a more rounded phenotype indicating start of cell death. At day 3 the number of caspase 3/7 positive cells (green) increase. At day 6 cancer cells with ad.CA.GSK3b are mostly positive for the apoptotic marker while cancer cells transduced with the control virus barely shows any apoptotic cells. SK-MEL-28 cell line data is shown as example.
Figure 2B:
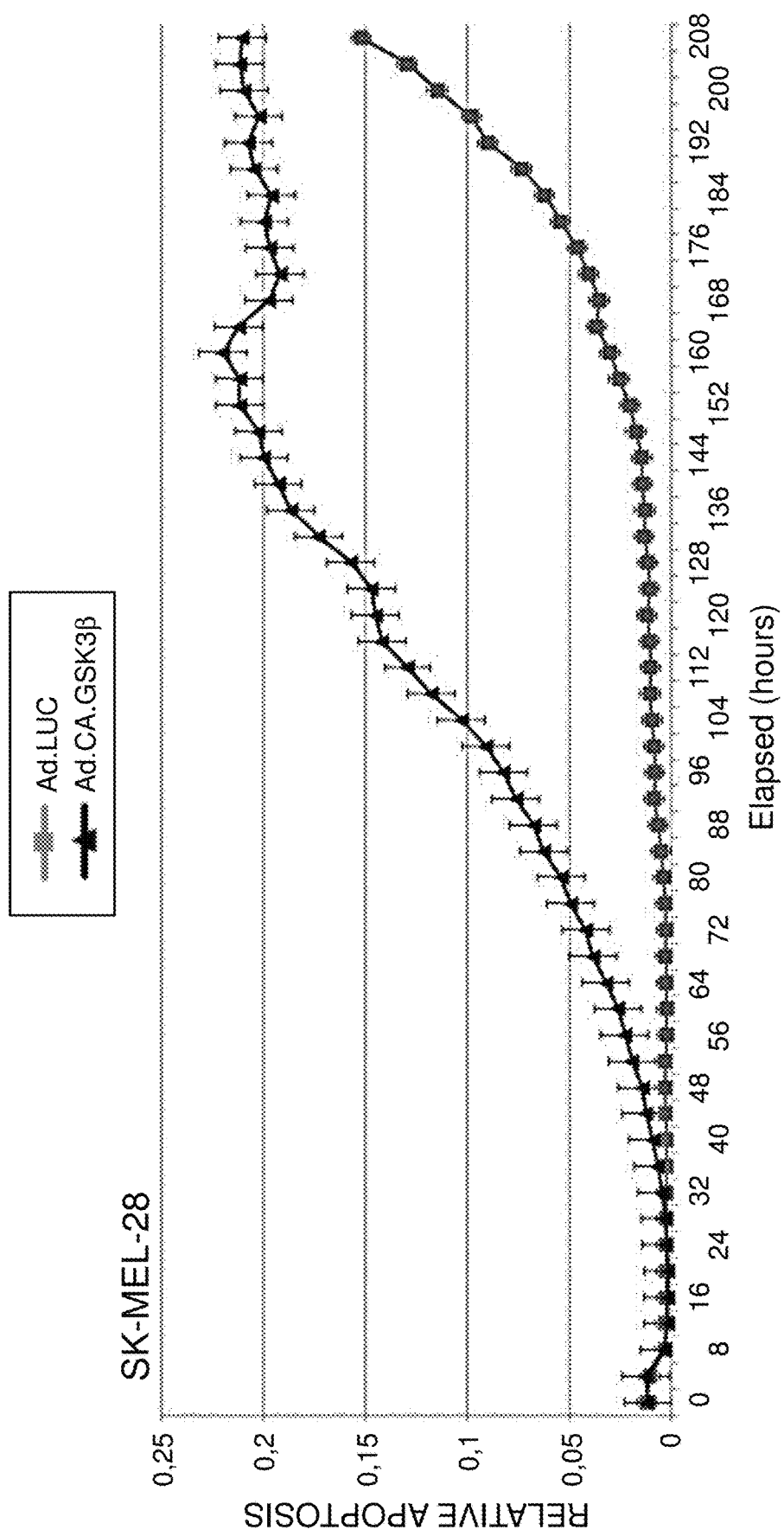
FIG. 2B Relative apoptosis of different melanoma cell lines at different time points comparing the effect of cells transduced with ad.LUC versus ad.CA.GSK3-beta. Ad.CA.GSK3-beta induces apoptosis earlier than Ad.Luc, demonstrating the oncolytic effect of infecting melanoma cells with an adenovirus expressing the constitutively active form of GSK3-beta.
Figure 5:
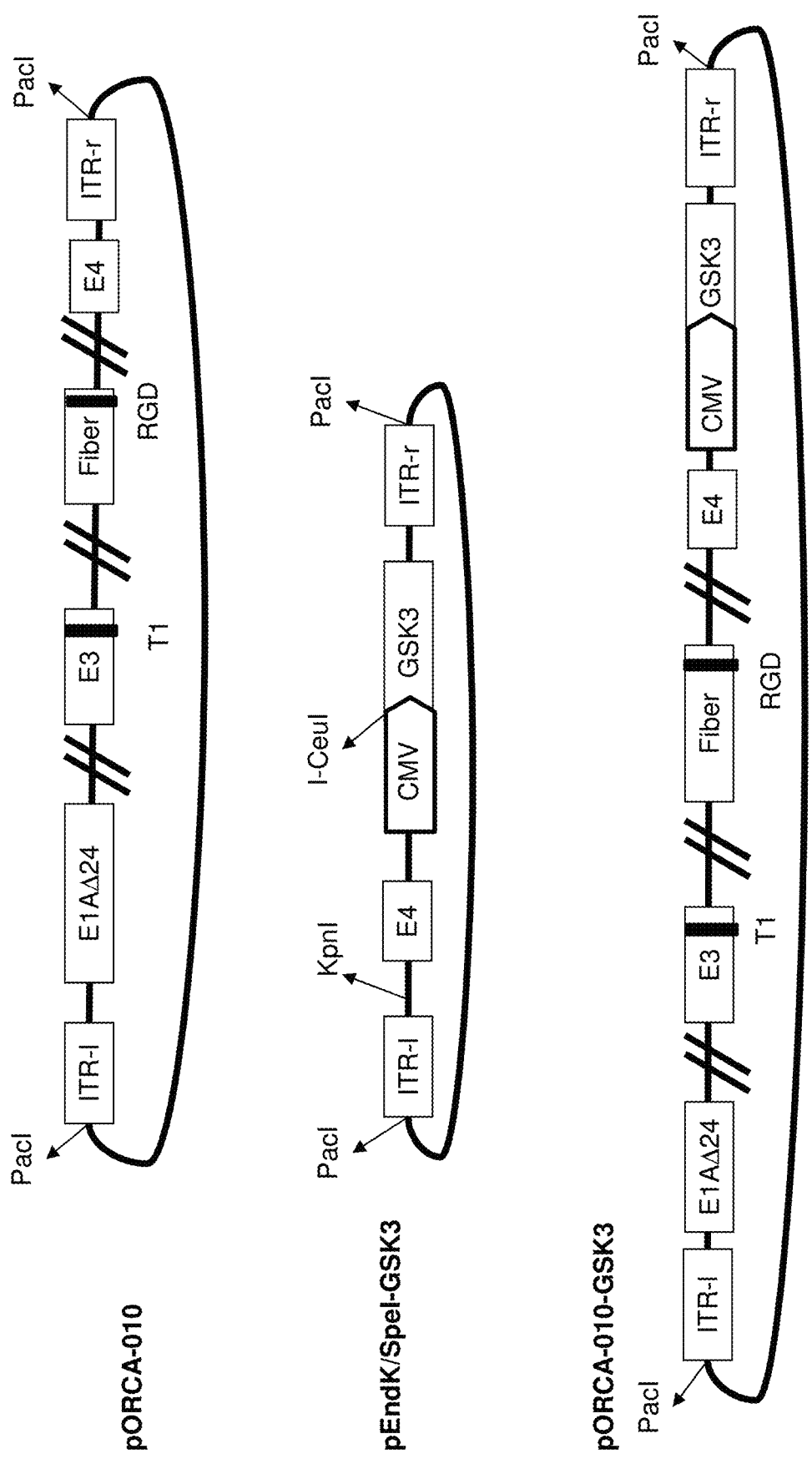
FIG. 5. Schematic representation of the DNA construct coding for the ORCA-10 virus described in Dong et al. (2014, Human Gene Therapy 25: 897-904), a schematic representation of a homologous recombination construct comprising a coding region for GSK3betaS9A under control of a CMV promoter; and a schematic representation of the recombined construct comprising the ORCA-10 virus with the coding region for GSK3betaS9A under control of a CMV promoter.
Figure 6:
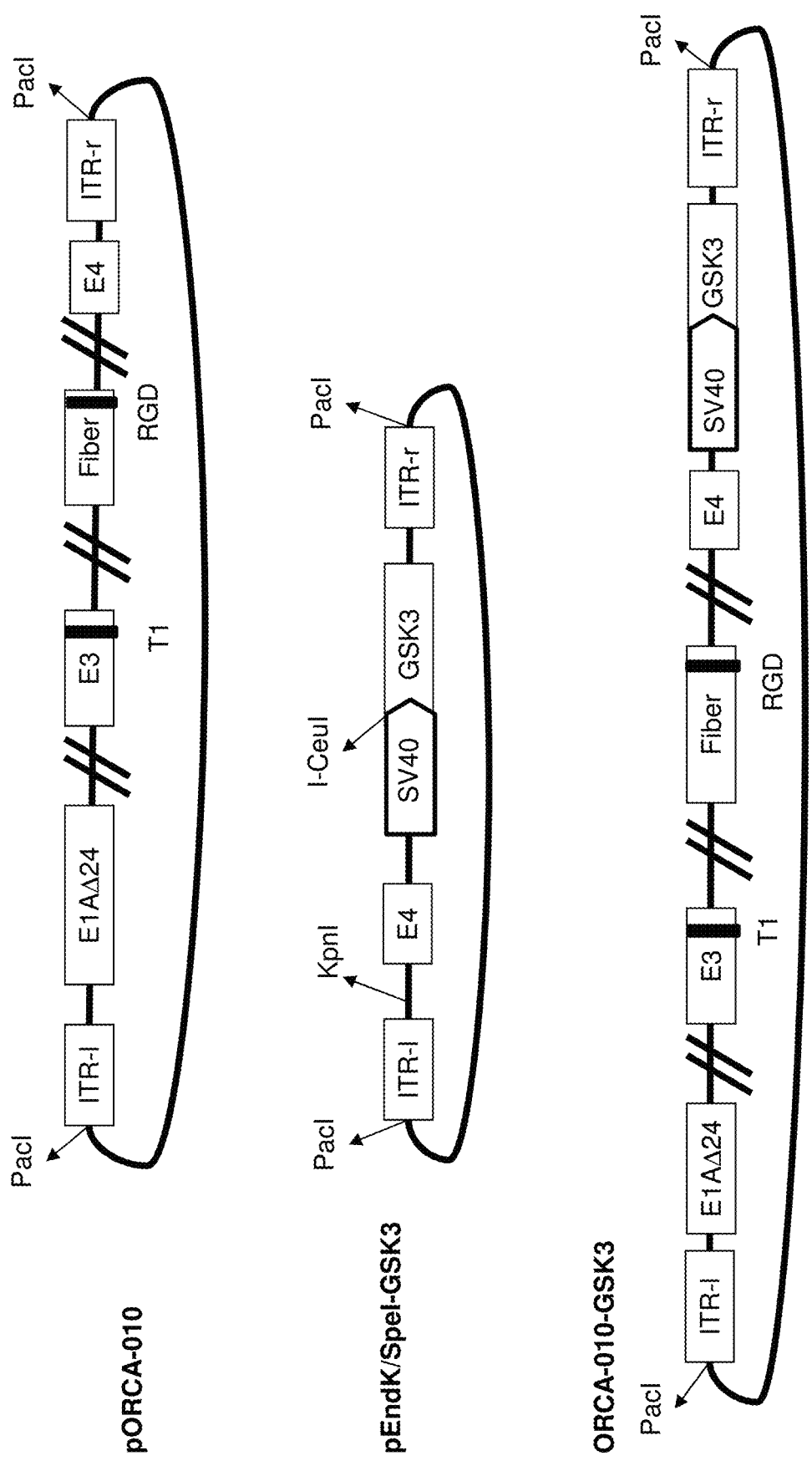
FIG. 6. Schematic representation of the DNA construct coding for the ORCA-10 virus described in Dong et al. (2014, Human Gene Therapy 25: 897-904), a schematic representation of a homologous recombination construct comprising a coding region for GSK3betaS9A under control of an SV40 promoter; and a schematic representation of the recombined construct comprising the ORCA-10 virus with the coding region for GSK3betaS9A under control of the SV40 promoter.
Figure 7:
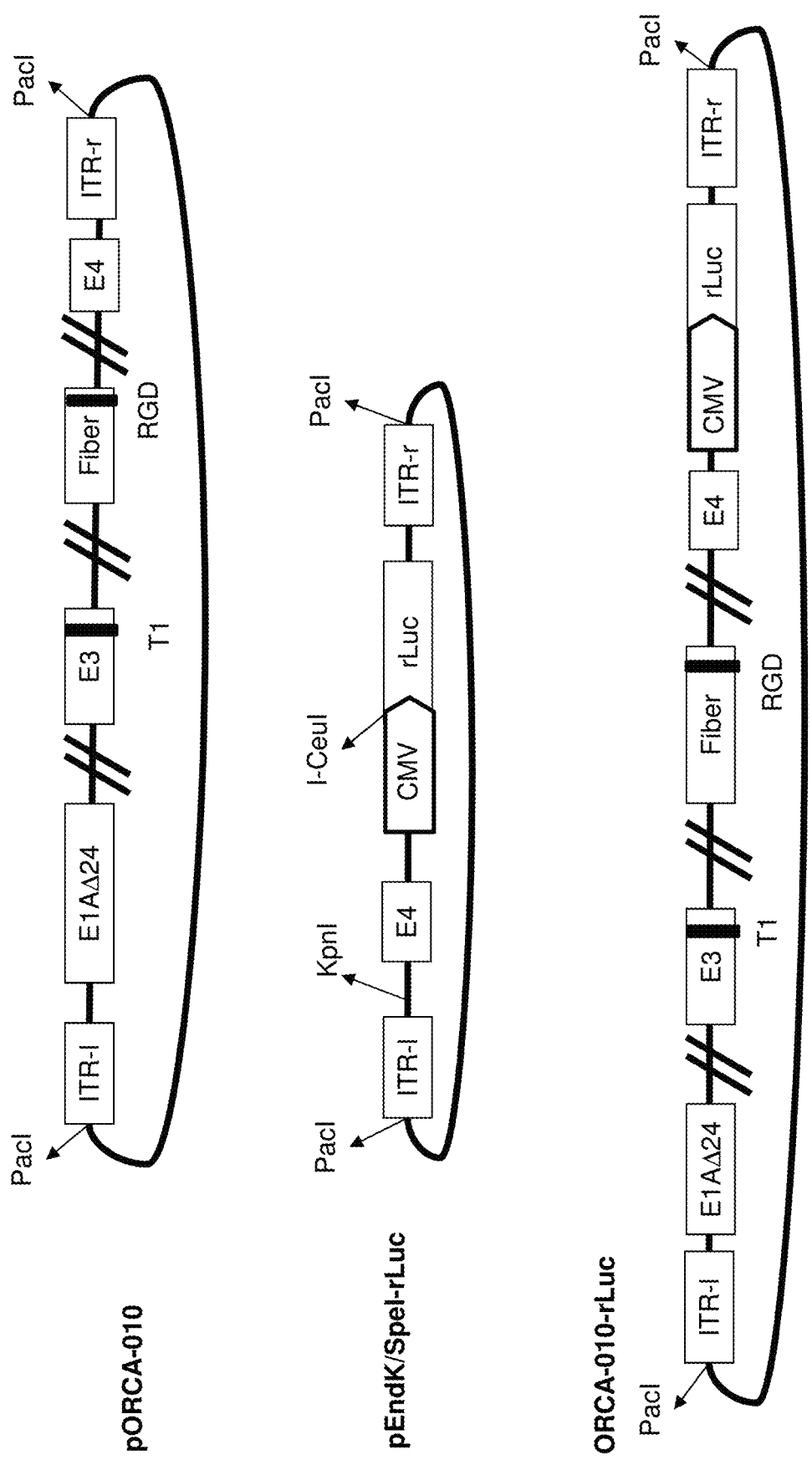
FIG. 7. Schematic representation of the DNA construct coding for the ORCA-10 virus described in Dong et al. (2014, Human Gene Therapy 25: 897-904), a schematic representation of a homologous recombination construct comprising a coding region for rLuc, a luciferase coding region under control of a CMV promoter; and a schematic representation of the recombined construct comprising the ORCA-10 virus with the coding region for rLuc under control of the mentioned CMV promoter.

Over a period of 6 days, the percentage of caspase3/7 positive cells (apoptotic cells) increased more rapidly in cultures infected with Ad.CA.GSK3-beta compared to Ad.LUC infected cultures (FIGS. 2A and B); On day 1, there is a clear effect on the morphology of the SK-MEL-28 cells when infected with the Ad.CA.GSK3-beta in contrast with the control virus (Ad.LUC) (FIG. 2A). At day 3, several caspase 3/7 positive stained cells can be observed in the cultures with AdcAGSK3-beta (indicated with the green label).

At day 6, SK-MEL-28 transduced with Ad.CA.GSK3-beta are mostly positive for the apoptotic marker while the cancer cells transduced with the control virus barely show any apoptotic cells.

These data demonstrated that the adenoviral enforced expression of a constitutively active form of GSK3-beta promotes apoptosis of cancer cells.

Example 3. GSK3-Beta Expressing Adenovirus Induces Selective Cancer Cell Killing in Metastatic Melanoma Tumor Suspensions To demonstrate the anti-tumor effect of adenoviral delivered GSK3-beta, metastatic melamoma tumor cell suspensions were infected with Ad.LUC or Ad.CA.GSK3-beta.

Viable tumor tissue was obtained from melanoma patients. Samples were then minced with scalpels, and dissociated in HBSS (Whittaker Bioproducts) with 0.1% DNase type I and 0.14% collagenase type I (Sigma Chemical). Single-cell suspensions were then frozen with 10% DMSO in a controlled-rate freezer in aliquots of 15 to 20 million cells per mL and stored in liquid nitrogen until use.

The melanoma cell-suspensions were thawed, and 1.200.000 metastatic melanoma tumor cells were cultured in complete RPMI in a 6 well plate and infected 4 hours later with 500 MOI of Ad.LUC or Ad.CA.GSK3-beta. Cells were then incubated for 5 days at 37° C. and 5% CO2. After 5 days, samples were harvested (centrifugation at 1560 rpm for 5 min) and washed with PBS supplemented with 0.1% bovine serum albumin (BSA) and 0.02% sodium azide and 0.1% BSA in PBS (FACS buffer) and centrifuged for 5 minutes at 1560 rpm. Next, supernatants were removed leaving the cell pellet in approximately 50 microliters of supernatant. Cells were resuspended in the remaining supernatant and stained for the surface markers CD45 (AF700, Biolegend) and MCSP (APC, Miltenyi biotec) for 30 minutes at 4° C. After incubation, the excess of antibodies was removed by washing with FACS buffer. Samples were analyzed by the flow cytometer Fortessa (BD Bioscience) and the Kaluza analysis software (Beckman).

The results of this analysis are shown in FIG. 3. Cells were stained with the CD45 marker to distinguish melanoma cells from healthy immune cells in the tumor microenvironment. Immune cells (gated in purple) are positive for CD45 while tumor cells are negative. In addition, to really discriminate between cancer cells and non-immune healthy cells (such as fibroblasts), MCSP marker was added. MCSP is a known melanoma marker, therefore, melanoma cells will be MCSP+CD45− cells (gated in orange). Nevertheless, it is important to notice that the MCSP-CD45− cell fraction (gated in blue), could contain both non-immune healthy cells but perhaps also some melanoma cells that don't express the MCSP marker (not all melanoma cells are positive for the same marker and there is donor variability in this regard).

When the melanoma cell suspension was transduced with the Ad.CA.GSK3-beta, the relative percentage of melanoma cells after 5 days was 1.72%. In contrast, in the Ad.LUC infected melanoma suspension the relative percentage of surviving melanoma cells was 21.65%. Moreover, the immune cells appeared to remain unaffected by the presence of Ad.CA.GSK3-beta, with 50.77% survival with Ad.LUC and 64.29% with Ad.CA.GSK3-beta, demonstrating further the tumor specificity of Ad.CA.GSK3-beta. Other cells (the CD45-MCSP−, mostly healthy non-immune cells, like fibroblasts) were also not affected by the transduction with the adenovirus coding for constitutively active GSK3-beta.

The results show the potential to exploit the adenoviral delivery of constitutively active GSK3-beta to induce specific cancer cell killing.

Example 4. Expression of GSK3-Beta Enhances Adenoviral Replication

Ad.CA.GSK3-beta and Ad.LUC are replication deficient adenoviral vectors. In order to validate the effect of the constitutively active GSK3-beta in the context of a replication competent adenovirus, an experiment in 911 cells (a cell line that complements replication deficient adenoviruses for adenoviral replication) was performed (FIG. 4). Replication deficient Ad.LUC or Ad.CA.GSK3-beta were amplified in 911 cells (a cell line that complements for adenoviral replication). 911 cells (Fallaux F J et al. Hum Gene Ther., (1992): 215-22) were cultured in complete RPMI. On day 1, 911 cells were plated in a 96-well plate (10 000 cells/well) and infected 6 hours later with ad.LUC or ad.CA.GSK3-beta at MOI 1. As negative infection control, uninfected 911 cells were used. Cells were incubated at 37° C. and 5% CO2 in the IncuCyte Zoom and followed for 5 days. Pictures of the wells were taken at different intervals by the IncuCyte.

The results demonstrate that Ad.LUC induced visible CPE (cytopathic effect) at approximately 3 days post infection (FIG. 4B), while the GSK3-beta expressing virus (Ad.CA.GSK3-beta) displays CPE already at day 1 (FIG. 4C), demonstrating a synergistic cytotoxic effect of GSK3-beta and replication competent adenovirus. The MOI used in this experiment was 1 infectious viral particle per cell (1 MOI). Therefore, most probably, not all cells are infected by a viral particle from the inoculum. Taken together with the lack of cellular proliferation in the Ad.CA.GSK3-beta infected cells, this indicates that the presence of constitutively active GSK3-beta accelerates viral replication or viral release, desirable characteristics for oncolytic viral therapies.

Example 5. A Method to Construct Replication Competent Adenoviruses Expressing GSK3-Beta A replication competent adenovirus containing GSK3b between the E4 and right-hand ITR of the adenovirus genome different cloning steps can be made as follows. An adenovirus shuttle vector carrying the GSK3b expression cassette is made. In a second step this shuttle vector is linearized and recombined with full length linearized adenovirus DNA (e.g. ORCA-010; i.e., an oncolytic adenovirus with the E1AA24, T1 mutation and fiber RGD insertion). The GSK3-beta DNA sequence will contain a serine 9 to alanine mutation and a HA (haemaglutinin) tag sequence at the C-terminal region.

GSK3-Beta Expression Cassette

The GSK3-beta expression cassette contains below sequences. The expression cassette is generated by DNA synthesis (GeneArt Gene Synthesis, ThermoFisher Scientific). The expression cassette is cloned into a pMK cloning vector (ThermoFisher Scientific) using the EcoRI restriction site.

```
CMV-GSK3-betaHA-pA
EcoRI site
GAATTC-

SpeI site
ACTAGT-

CMV enhancer
GACATTGATTATTGACAGTTATTAATAGTAATCAATTACGGGGTCATTA
GTTCATAGCCCATATATGGAGTTCCGCGTTACATAACTTACGGTAAATG
GCCCGCCTGGCTGACCGCCCAACGACCCCCGCCCATTGACGTCAATAAT
GACGTATGTTCCCATAGTAACGCCAATAGGGACTTTCCATTGACGTCAA
TGGGTGGACTATTTACGGTAAACTGCCCACTTGGCAGTACATCAAGTGT
ATCATATGCCAAGTACGCCCCCTATTGACGTCAATGACGGTAAATGGCC
CGCCTGGCATTATGCCCAGTACATGACCTTATGGGACTTTCCTACTTGG
CAGTACATCTACGTATTAGTCATCGCTATTACCATG- CMV promotor
GTGATGCGGTTTTGGCAGTACATCAATGGGCGTGGATAGCGGTTTGACT
CACGGGGATTTCCAAGTCTCCACCCCATTGACGTCAATGGGAGTTTGTT
TTGGCACCAAAATCAACGGGACTTTCCAAAATGTCGTAACAACTCCGCC
CCATTGACGCAAATGGGCGGTAGGCGTGTACGGTGGGAGGTCTATATAA
GCAGAGCT- Sequence containing I-CeuI restriction site
CGTAACTATAACGGTCCTAAGGTAGCGAAA- HA tagged GSK3 beta sequence (HA-tag sequence in
italic and underlined)
ATGGCAGGGCGGCCCAGAACCACCACCGCCTTTGCGGAGAGCTGCAAGCCGG
TGCAGCAGCCTTCAGCTTTTGGCAGCATGAAAGTTAGCAGAGACAAGGA
CGGCAGCAAGGTGACAACAGTGGTGGCAACTCCTGGGCAGGGTCCAGAC
AGGCCACAAGAAGTCAGCTATACAGACACTAAAGTGATTGGAAATGGAT
CATTTGGTGTGGTATATCAAGCCAAACTTTGTGATTCAGGAGAACTGGT
CGCCATCAAGAAAGTATTGCAGGACAAGAGATTTAAGAATCGAGAGCTC
CAGATCATGAGAAAGCTAGATCACTGTAACATAGTCCGATTGCGTTATT
TCTTCTACTCCAGTGGTGAGAAGAAAGATGAGGTCTATCTTAATCTGGT
GCTGGACTATGTTCCGGAAACAGTATACAGAGTTGCCAGACACTATAGT
CGAGCCAAACAGACGCTCCCTGTGATTTATGTCAAGTTGTATATGTATC
AGCTGTTCCGAAGTTTAGCCTATATCCATTCCTTTGGAATCTGCCATCG
GGATATTAAACCGCAGAACCTCTTGTTGGATCCTGATACTGCTGTATTA
AAACTCTGTGACTTTGGAAGTGCAAAGCAGCTGGTCCGAGGAGAACCCA
ATGTTTCGTATATCTGTTCTCGGTACTATAGGGCACCAGAGTTGATCTT
TGGAGCCACTGATTATACCTCTAGTATAGATGTATGGTCTGCTGGCTGT
GTGTTGGCTGAGCTGTTACTAGGACAACCAATATTTCCAGGGGATAGTG
GTGTGGATCAGTTGGTAGAAATAATCAAGGTCCTGGGAACTCCAACAAG
GGAGCAAATCAGAGAAATGAACCCAAACTACACAGAATTTAAATTCCCT
CAAATTAAGGCACATCCTTGGACTAAGGTCTTCCGACCCCGAACTCCAC
CGGAGGCAATTGCACTGTGTAGCCGTCTGCTGGAGTATACACCAACTGC
CCGACTAACACCACTGGAAGCTTGTGCACATTCATTTTTTGATGAATTA
CGGGACCCAAATGTCAAACATCCAAATGGGCGAGACACACCTGCACTCT
TCAACTTCACCACTCAAGAACTGTCAAGTAATCCACCTCTGGCTACCAT
CCTTATTCCTCCTCATGCTCGGATTCAAGCAGCTGCTTCAACCCCCACA
AATGCCACAGCAGCGTCAGATGCTAATACTGGAGACCGTGGACAGACCA
ATAATGCTGCTTCTGCATCAGCTTCCAACTCCACTAGC*TACCCATACGA*
*TGTTCCAGATTACGCA*AAGCTTGGGTGGTCCCAACTAApolyA
TGGATCCAGACATGATAAGATACATTGATGAGTTTGGACAAACCACAAC
TAGAATGCAGTGAAAAAAATGCTTTATTTGTGAAATTTGTGATGCTATT
GCTTTATTTGTAACCATTATAAGCTGCAATAAACAAGTTAACAACAACA
ATTGCATTCATTTTATGTTTCAGGTTCAGGGGGAGGTGTGGGAGGTTTT
TTAAAGCAAGTAAAACCTCTACAAATGTGATATGGCTGAT- SpeI site
ACTAGT EcoRI site
GAATTC-
```

Shuttle Vector Carrying the GSK3-Beta Expression Cassette Construction

As shuttle vector backbone the pEndK/Spel vector (provided by Dr. R. Alemany, Institut Catala d'Oncologia, Barcelona, Spain) will be used. (pEndK/Spel was made by KpnI digestion of the vector pTG3602 (Chartier et al., J. Virol, 70(1996):4805-4810) and religation of the vector fragment comprising Ad5 map units 0-7 and 93-100 to create pEndK. A SpeI site was introduced into pEndK by changing Ad5 nucleotide 35813 from A to T by site directed mutagenesis to create pEndK/SpeI. pEndK/SpeI carries PacI restriction sites flanking the two Ad5 ITRs.

The GSK3-beta expression cassette generated by DNA synthesis is cloned into the pEndK/SpeI using the SpeI restriction site, resulting in pEndK/SpeI-GSK3beta. Correct pEndK/SpeI-GSK3-beta clones can be identified by restriction analysis using different restriction enzymes present in the vector (e.g. I-CeuI unique restriction site).

Recombination to Generate a Full-Length Adenovirus Genome Carrying GSK3-Beta

The plasmid pEndK/SpeI-GSK3beta is linearized with KpnI. The linearized plasmid can be recombined in bacteria (e.g. BJ5183) or yeast (e.g. YPH857), with full-length replication competent adenovirus DNA (e.g. ORCA-010).

The full-length adenovirus DNA can be isolated from adenovirus particles or, alternatively, can be released by restriction enzyme digestion from a plasmid carrying a full-length adenovirus DNA insert.

Homologous recombination creates a plasmid with a full-length adenovirus genome, in which the GSK3-beta expression cassette is inserted between the E4 region and the right-hand ITR. It should be noted that any replication competent adenovirus can be used to insert the GSK3b expression cassette according to this method, including recombinant adenoviruses with additional modifications, such as e.g. E3 deleted, enhanced tumor-selectivity or oncolytic potential, a changed tropism or transgene insertion. It is preferred, however, that said full-length replication competent adenovirus genome does not include a PacI restriction site in its genome.

Virus Generation

The replication competent adenovirus genome with inserted GSK3b expression cassette is subsequently released from the plasmid by PacI digestion. This DNA is transfected into human cells, e.g., A549 cultured in Dulbecco's modified Eagle medium supplemented with 10% FBS (Hyclone) and 100 U/mL Pen/Strep using, e.g., lipofectamine reagent. The resulting recombinant replication competent adenovirus according to the invention is isolated and further propagated and purified according to standard cell culture and virology methods known in the art.

Example 6. A Method to Construct Replication Competent Adenoviruses Expressing GSK3-Beta Similar to example 5, where the GSK3-beta expression cassette has the sequence below.

SV40-GSK3-betaHA-pA
EcoRI site
GAATTC-

SpeI site
ACTAGT-

SV40 promoter
GGTGTGGAAAGTCCCCAGGCTCCCCAGCAGGCAGAAGTATGCAAAGCAT
GCATCTCAATTAGTCAGCAACCAGGTGTGGAAAGTCCCCAGGCTCCCCA
GCAGGCAGAAGTATGCAAAGCATGCATCTCAATTAGTCAGCAACCATAG
TCCCGCCCCTAACTCCGCCCATCCCGCCCCTAACTCCGCCCAGTTCCGC
CCATTCTCCGCCCCATGGCTGACTAATTTTTTTTATTTATGCAGAGGCC
GAGGCCGCCTCGGCCTCTGAGCTATTCCAGAAGTAGTGAGGAGGCTTTT
TTGGAGGCCTAGGCTTTTGCAAA- Sequence containing I-CeuI restriction site
CGTAACTATAACGGTCCTAAGGTAGCGAAA- HA tagged GSK3 beta sequence (HA-tag sequence in italic and underlined)

-continued
ATGGCAGGGCGGCCCAGAACCACCGCCTTTGCGGAGAGCTGCAAGCCGG
TGCAGCAGCCTTCAGCTTTTGGCAGCATGAAAGTTAGCAGAGACAAGGA
CGGCAGCAAGGTGACAACAGTGGTGGCAACTCCTGGGCAGGGTCCAGAC
AGGCCACAAGAAGTCAGCTATACAGACACTAAAGTGATTGGAAATGGAT
CATTTGGTGTGGTATATCAAGCCAAACTTTGTGATTCAGGAGAACTGGT
CGCCATCAAGAAAGTATTGCAGGACAAGAGATTTAAGAATCGAGAGCTC
CAGATCATGAGAAAGCTAGATCACTGTAACATAGTCCGATTGCGTTATT
TCTTCTACTCCAGTGGTGAGAAGAAAGATGAGGTCTATCTTAATCTGGT
GCTGGACTATGTTCCGGAAACAGTATACAGAGTTGCCAGACACTATAGT
CGAGCCAAACAGACGCTCCCTGTGATTTATGTCAAGTTGTATATGTATC
AGCTGTTCCGAAGTTTAGCCTATATCCATTCCTTTGGAATCTGCCATCG
GGATATTAAACCGCAGAACCTCTTGTTGGATCCTGATACTGCTGTATTA
AAACTCTGTGACTTTGGAAGTGCAAAGCAGCTGGTCCGAGGAGAACCCA
ATGTTTCGTATATCTGTTCTCGGTACTATAGGGCACCAGAGTTGATCTT
TGGAGCCACTGATTATACCTCTAGTATAGATGTATGGTCTGCTGGCTGT
GTGTTGGCTGAGCTGTTACTAGGACAACCAATATTTCCAGGGGATAGTG
GTGTGGATCAGTTGGTAGAAATAATCAAGGTCCTGGGAACTCCAACAAG
GGAGCAAATCAGAGAAATGAACCCAAACTACACAGAATTTAAATTCCCT
CAAATTAAGGCACATCCTTGGACTAAGGTCTTCCGACCCCGAACTCCAC
CGGAGGCAATTGCACTGTGTAGCCGTCTGCTGGAGTATACACCAACTGC
CCGACTAACACCACTGGAAGCTTGTGCACATTCATTTTTTGATGAATTA
CGGGACCCAAATGTCAAACATCCAAATGGGCGAGACACACCTGCACTCT
TCAACTTCACCACTCAAGAACTGTCAAGTAATCCACCTCTGGCTACCAT
CCTTATTCCTCCTCATGCTCGGATTCAAGCAGCTGCTTCAACCCCCACA
AATGCCACAGCAGCGTCAGATGCTAATACTGGAGACCGTGGACAGACCA
ATAATGCTGCTTCTGCATCAGCTTCCAACTCCACTAGC*TACCCATACGA*
*TGTTCCAGATTACGCA*AAGCTTGGGTGGTCCCAACTAApolyA
TGGATCCAGACATGATAAGATACATTGATGAGTTTGGACAAACCACAAC
TAGAATGCAGTGAAAAAAATGCTTTATTTGTGAAATTTGTGATGCTATT
GCTTTATTTGTAACCATTATAAGCTGCAATAAACAAGTTAACAACAACA
ATTGCATTCATTTTATGTTTCAGGTTCAGGGGGAGGTGTGGGAGGTTTT
TTAAAGCAAGTAAAACCTCTACAAATGTGATATGGCTGAT- SpeI site
ACTAGT EcoRI site
GAATTC- Example 7. A Method to Construct Replication Competent Adenoviruses Expressing Luciferase As control a luciferase expressing conditionally replication competent oncolytic adenovirus can be made. Methodology is similar to example 5 or 6, where the DNA synthesized HA tagged GSK3-beta sequence in the expression cassette has been replaced by the luciferase sequence below.

Renilla luciferase sequence
ATGACTTCGAAAGTTTATGATCCAGAACAAAGGAAACGGATGATAACTG

GTCCGCAGTGGTGGGCCAGATGTAAACAAATGAATGTTCTTGATTCATT

TATTAATTATTATGATTCAGAAAAACATGCAGAAAATGCTGTTATTTTT

TTACATGGTAACGCGGCCTCTTCTTATTTATGGCGACATGTTGTGCCAC

ATATTGAGCCAGTAGCGCGGTGTATTATACCAGACCTTATTGGTATGGG

CAAATCAGGCAAATCTGGTAATGGTTCTTATAGGTTACTTGATCATTAC

AAATATCTTACTGCATGGTTTGAACTTCTTAATTTACCAAAGAAGATCA

TTTTTGTCGGCCATGATTGGGGTGCTTGTTTGGCATTTTATTATAGCTA

TGAGCATCAAGATAAGATCAAAGCAATAGTTCACGCTGAAAGTGTAGTA

GATGTGATTGAATCATGGGATGAATGGCCTGATATTGAAGAAGATATTG

CGTTGATCAAATCTGAAGAAGGAGAAAAAATGGTTTTGGAGAATAACTT

CTTCGTGGAAACCATGTTGCCATCAAAAATCATGAGAAAGTTAGAACCA

GAAGAATTTGCAGCATATCTTGAACCATTCAAAGAGAAAGGTGAAGTTC

```
-continued
GTCGTCCAACATTATCATGGCCTCGTGAAATCCCGTTAGTAAAAGGTGG

TAAACCTGACGTTGTACAAATTGTTAGGAATTATAATGCTTATCTACGT

GCAAGTGATGATTTACCAAAAATGTTTATTGAATCGGACCCAGGATTCT

TTTCCAATGCTATTGTTGAAGGTGCCAAGAAGTTTCCTAATACTGAATT

TGTCAAAGTAAAGGTCTTCATTTTTCGCAAGAAGATGCACCTGATGAA

ATGGGAAAATATATCAAATCGTTCGTTGAGCGAGTTCTCAAAAATGAAC

AATAA
```

Example 8. A Method to Evaluate the Oncolytic Potency of GSK3-Beta Expressing Replication Competent Adenoviruses Oncolytic potency of GSK3-beta expressing replication competent adenoviruses generated in examples 5 and 6 will be compared with its relevant control (based on promoter), a luciferase expressing replication competent adenovirus generated in example 7. Alternatively, also other already available conditionally replication competent full length adenoviruses expressing luciferase under a CMV or SV40 promoter can be used.

To compare the oncolytic potency of the different viruses cytotoxicity assays on human cancer cell lines will be performed. Different cancer cell lines can be used for the assay (e.g. Hep3B, A549, U2OS, HCT 116, SK-MEL-28, UM-SCC-22A, LNCaP, NP9, DU-145, UM-SCC-11B, UM-SCC-14C, PC-3, VU1131, MDA-MB-231 and/or FaDu). Cytotoxicity assays will be performed according to Dong et al. (Human Gene Therapy 25 (2014): 897-904) using the viruses generated in examples 5, 6 and 7.

This work was funded in part by European Union Horizon 2020 research and innovation programme, Marie Sklodowska-Curie grant number 643130.

CITED ART

1. Beurel E, Grieco S F, Jope R S. 2015. Glycogen synthase kinase-3 (GSK-3): regulation, actions, and diseases. Pharmacol Ther 148: 114-31
2. Domoto T, Pyko I V, Furuta T, Miyashita K, Uehara M, Shimasaki T, Nakada M, Minamoto T. 2016. Glycogen synthase kinase-3beta is a pivotal mediator of cancer invasion and resistance to therapy. Cancer Sci 107: 1363-72
3. Stamos J L, Chu M L, Enos M D, Shah N, Weis W I. 2014. Structural basis of GSK-3 inhibition by N-terminal phosphorylation and by the Wnt receptor LRP6. Elife 3: e01998
4. Goc A, Al-Husein B, Katsanevas K, Steinbach A, Lou U, Sabbineni H, DeRemer D L, Somanath P R. 2014. Targeting Src-mediated Tyr216 phosphorylation and activation of GSK-3 in prostate cancer cells inhibit prostate cancer progression in vitro and in vivo. Oncotarget 5: 775-87
5. Nagini S, Sophia J, Mishra R. 2018. Glycogen synthase kinases: Moonlighting proteins with theranostic potential in cancer. Semin Cancer Biol
6. Li C H, Liu C W, Tsai C H, Peng Y J, Yang Y H, Liao P L, Lee C C, Cheng Y W, Kang J J. 2017. Cytoplasmic aryl hydrocarbon receptor regulates glycogen synthase kinase 3 beta, accelerates vimentin degradation, and suppresses epithelial-mesenchymal transition in non-small cell lung cancer cells. Arch Toxicol 91: 2165-78
7. Pramanik K K, Singh A K, Alam M, Kashyap T, Mishra P, Panda A K, Dey R K, Rana A, Nagini S, Mishra R. 2016. Reversion-inducing cysteine-rich protein with Kazal motifs and its regulation by glycogen synthase kinase 3 signaling in oral cancer. Tumour Biol 37: 15253-64
8. Yu L, Li X, Li H, Chen H, Liu H. 2016. Rab11a sustains GSK-3beta/Wnt/beta-catenin signaling to enhance cancer progression in pancreatic cancer. Tumour Biol 37: 13821-9
9. Furuta T, Sabit H, Dong Y, Miyashita K, Kinoshita M, Uchiyama N, Hayashi Y, Minamoto T, Nakada M. 2017. Biological basis and clinical study of glycogen synthase kinase-3beta-targeted therapy by drug repositioning for glioblastoma. Oncotarget 8: 22811-24
10. Garcea G, Manson M M, Neal C P, Pattenden C J, Sutton C D, Dennison A R, Berry D P. 2007. Glycogen synthase kinase-3 beta; a new target in pancreatic cancer?Curr Cancer Drug Targets 7: 209-15
11. Ma C, Wang J, Gao Y, Gao T W, Chen G, Bower K A, Odetallah M, Ding M, Ke Z, Luo J. 2007. The role of glycogen synthase kinase 3beta in the transformation of epidermal cells. Cancer Res 67: 7756-64
12. Farago M, Dominguez I, Landesman-Bollag E, Xu X, Rosner A, Cardiff R D, Seldin D C. 2005. Kinase-inactive glycogen synthase kinase 3beta promotes Wnt signaling and mammary tumorigenesis. Cancer Res 65: 5792-801
13. Mishra R, Nagini S, Rana A. 2015. Expression and inactivation of glycogen synthase kinase 3 alpha/beta and their association with the expression of cyclin D1 and p53 in oral squamous cell carcinoma progression. Mol Cancer 14: 20
14. Zhou W, Wang L, Gou S M, Wang T L, Zhang M, Liu T, Wang C Y. 2012. ShRNA silencing glycogen synthase kinase-3 beta inhibits tumor growth and angiogenesis in pancreatic cancer. Cancer Lett 316: 178-86
15. Shakoori A, Mai W, Miyashita K, Yasumoto K, Takahashi Y, Ooi A, Kawakami K, Minamoto T. 2007. Inhibition of GSK-3 beta activity attenuates proliferation of human colon cancer cells in rodents. Cancer Sci 98: 1388-93
16. Kingwell K. 2018. Flipping the switch for selective GSK-3 inhibition. Nature Reviews Drug Discovery 17: 314
17. Krasnykh V., Belousova N., Korokhov N., Mikheeva G., Curiel D. T. Genetic targeting of an adenovirus vector via replacement of the fiber protein with the phage T4 fibritin. J. of Virology., 75: 4176-4183, 2001.
18. Kim H. S., Skurk C., Thomas S. R., Bialik A., Suhara T., Kureishi Y., Birnbaum M., Keaney J. F. Regulation of Angiogenesis by Glycogen Synthase Kinase-3. J. of Biological Chemistry, 277: 41888-41896, 2002.

The invention claimed is:

1. A recombinant replication competent adenovirus comprising in the genome of the adenovirus a coding sequence for a glycogen synthase kinase-3 (GSK3) protein operably linked to an expression control sequence, wherein the replication competent adenovirus comprises a modification that enables preferential replication of the adenovirus in tumor cells, and wherein the modification comprises:
   a mutation in E1A gene, E1B gene or in both genes, and
   a promoter for tumor specific expression of E1A or E1B, or a promoter for tissue or cell type specific expression of E1A or E1B.

2. The adenovirus of claim 1, comprising a modification of a nucleic acid sequence in the E3 region.

3. The adenovirus of claim 1, wherein the adenovirus is an oncolytic adenovirus.

4. The adenovirus of claim 1, wherein the GSK3 protein is a GSK3-beta protein.

5. The adenovirus of claim 1, wherein the GSK3 protein is a mutant protein that is constitutively active.

6. A method for treating cancer in an individual comprising administering to the individual in need thereof the adenovirus of claim 1, or the adenovirus of claim 1 and a further medicament.

7. A method of killing a cancer cell comprising providing the cancer cell with the adenovirus of claim 1, or the adenovirus of claim 1 and a further medicament.

8. A method for enhancing the rate of replication of a recombinant replication competent adenovirus in a permissive cell comprising providing the genome of said adenovirus with a coding sequence for a GSK3 protein operably linked to an expression control sequence for expressing said coding sequence in said cell, wherein the replication competent adenovirus comprises a modification that enables preferential replication of the adenovirus in tumor cells, and wherein the modification comprises:
   a mutation in E1A gene, E1B gene or in both genes, and
   a promoter for tumor specific expression of E1A or E1B, or a promoter for tissue or cell type specific expression of E1A or E1B.

9. A method for increasing an oncolytic property of an oncolytic recombinant replication competent adenovirus comprising providing the genome of said adenovirus with coding sequence for a GSK3 protein operably linked to an expression control sequence for expressing said coding sequence, wherein the replication competent adenovirus comprises a modification that enables preferential replication of the adenovirus in tumor cells, and wherein the modification comprises:
   a mutation in E1A gene, E1B gene or in both genes, and
   a promoter for tumor specific expression of E1A or E1B, or a promoter for tissue or cell type specific expression of E1A or E1B.

10. A method of increasing the rate of replication and spreading of a recombinant replication competent adenovirus in a tumor, the method comprising providing the oncolytic adenovirus with a coding sequence for a GSK3 protein operably linked to an expression control sequence for expressing said coding sequence in cells of said tumor, wherein the replication competent adenovirus comprises a modification that enables preferential replication of the adenovirus in tumor cells, and wherein the modification comprises:

a mutation in E1A gene, E1B gene or in both genes, and
a promoter for tumor specific expression of E1A or E1B,
or a promoter for tissue or cell type specific expression of E1A or E1B.

11. The adenovirus of claim 1, further comprising a coding region for IL2, GM-CSF and/or TNF-alpha.

12. A combination comprising the adenovirus of claim 1 and a further medicament.

13. The combination of claim 12, wherein the further medicament comprises an antibody.

14. The method of claim 6, further comprising administration of concurrent or sequential radiotherapy, antibody therapy, chemotherapy, cell-therapy, immunotherapy or other anticancer intervention or treatment.

15. The method of claim 6, wherein the medicament comprises an antibody.

* * * * *